(12) United States Patent
Yamaguchi et al.

(10) Patent No.: US 10,961,560 B2
(45) Date of Patent: Mar. 30, 2021

(54) TRYPTOPHAN OXIDASE AND USE THEREOF

(71) Applicant: AJINOMOTO CO., INC., Tokyo (JP)

(72) Inventors: Hiroki Yamaguchi, Kanagawa (JP); Kazutoshi Takahashi, Kanagawa (JP); Moemi Tatsumi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 40 days.

(21) Appl. No.: 16/293,794

(22) Filed: Mar. 6, 2019

(65) Prior Publication Data

US 2019/0185904 A1 Jun. 20, 2019

Related U.S. Application Data

(63) Continuation of application No. PCT/JP2017/032917, filed on Sep. 12, 2017.

(30) Foreign Application Priority Data

Sep. 12, 2016 (JP) .............................. JP2016-177995

(51) Int. Cl.
| | | |
|---|---|---|
| *C12N 15/09* | (2006.01) | |
| *C12Q 1/26* | (2006.01) | |
| *C12M 1/34* | (2006.01) | |
| *G01N 27/416* | (2006.01) | |
| *C12P 21/02* | (2006.01) | |
| *G01N 33/68* | (2006.01) | |
| *C12Q 1/00* | (2006.01) | |

(52) U.S. Cl.
CPC ................. *C12Q 1/26* (2013.01); *C12M 1/34* (2013.01); *C12N 15/09* (2013.01); *C12P 21/02* (2013.01); *C12Q 1/00* (2013.01); *G01N 27/416* (2013.01); *G01N 33/68* (2013.01); *C12Y 113/11011* (2013.01)

(58) Field of Classification Search
CPC ......... A61K 38/44; C12N 9/0004; C12Q 1/26
USPC ....................................................... 435/189
See application file for complete search history.

(56) References Cited

U.S. PATENT DOCUMENTS

| 9,695,460 B2 | 7/2017 | Asano et al. |
| 2013/0344526 A1 | 12/2013 | Asano et al. |

FOREIGN PATENT DOCUMENTS

| JP | 2012-196207 A | 10/2012 |
| JP | 2014-161258 A | 9/2014 |
| JP | 2015-023859 A | 2/2015 |
| WO | WO2012/121144 A1 | 9/2012 |
| WO | WO2016/039961 A1 | 3/2016 |

OTHER PUBLICATIONS

Fuller et al. [The Journal of Biological Chemistry vol. 291, No. 38, pp. 20068-20084, Published, JBC Papers in Press, Jul. 27, 2016]. (Year: 2016).*
Extended European Search Report for European Patent App. No. 17848914.2 (dated Feb. 24, 2020).
Puranik, S., "Tryptophan oxidase from Pseudogulbenkiania ferrooxidans EGD-HP2," Sep. 7, 2016, XP055668155, retrieved from the Internet: URL:https://www.uniprot.org/uniprot/U1AQ27.txt?version=13, retrieved on Feb. 13, 2020.
Kameya, M., et al., "Selective tryptophan determination using tryptophan oxidases involved in bis-indole antibiotic biosynthesis," Analytical Biochem. 2013;438(2):124-132.
Yamaguchi, H., et al., "Protein engineering for improving the thermostability of tryptophan oxidase and insights from structural analysis," J. Biochem. 2018;164(5):359-367.
Fuller, J. J., et al., "Biosynthesis of Violacein, Structure and Function of L-Tryptophan Oxidase VioA from Chromobacterium violaceum," J. Biol. Chem. 2016;291(38):20068-20084.
International Search Report and Written Opinion for PCT Patent App. No. PCT/JP2017/032917 (dated Dec. 12, 2017) with English translation of the ISR.

* cited by examiner

Primary Examiner — Tekchand Saidha
(74) Attorney, Agent, or Firm — Cermak Nakajima & McGowan LLP; Shelly Guest Cermak

(57) ABSTRACT

A mutated tryptophan oxidase suitable for practical implementation is described herein. Specifically, a mutated tryptophan oxidase wherein at least one amino acid residue of a wild-type tryptophan oxidase is mutated and, as a result, has higher tryptophan oxidase activity and/or stability as compared to the wild-type tryptophan oxidase. The mutated tryptophan oxidase can be derived from a wild-type tryptophan oxidase having at least one of Motifs (2), (3), (5), (7), (9), (11), (13), and (14), and at least one amino acid residue in any of these motifs can have mutation. The mutated tryptophan oxidase also can have a mutation of one or more amino acid residues in an amino acid sequence represented by SEQ ID NO: 2 and a sequence homologous thereto.

19 Claims, 1 Drawing Sheet
Specification includes a Sequence Listing.

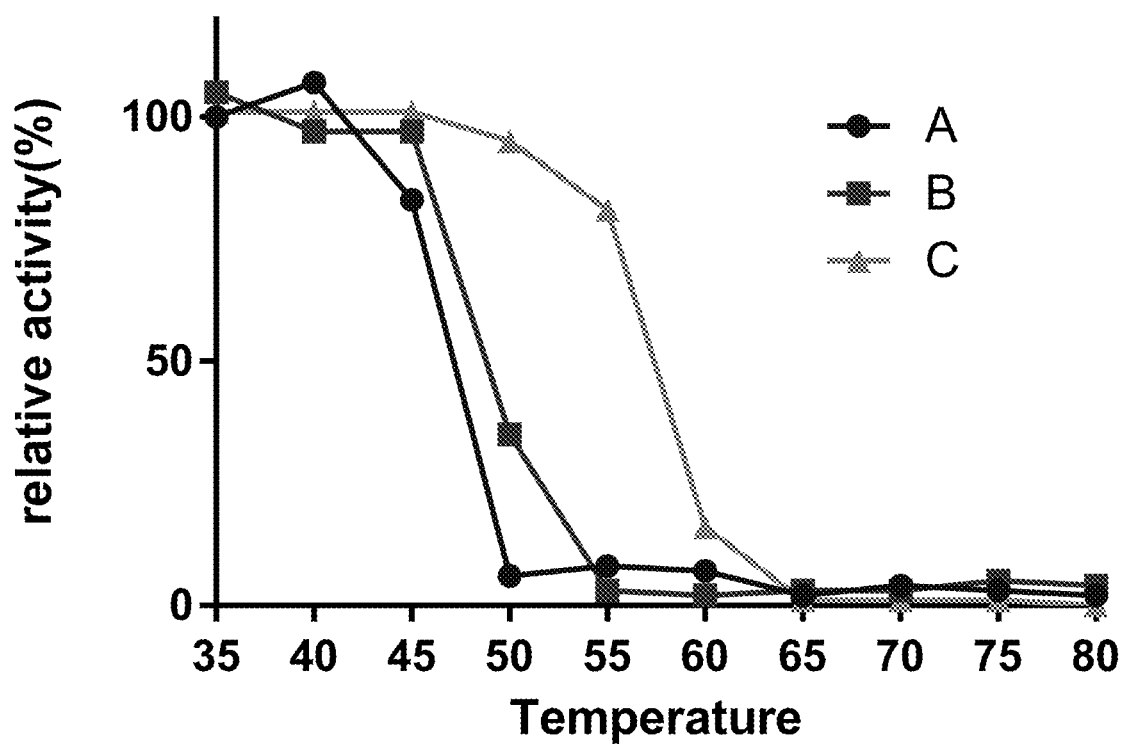

SEQUENCE LISTING

<160> NUMBER OF SEQ ID NOS: 4

<210> SEQ ID NO 1
<211> LENGTH: 1254
<212> TYPE: DNA
<213> ORGANISM: Chromobacterium violaceum

<400> SEQUENCE: 1

| | |
|---|---|
| atgaagcatt cttccgatat ctgcattgtc ggcgccggca tcagcggcct gacctgcgcc | 60 |
| agccatctgc tcgactcgcc cgcttgccgc ggcctgtcgc tgcgcatctt cgacatgcag | 120 |
| caggaggcgg gcggccgcat ccgctcgaag atgctggatg gcaaggcgtc gatagagctg | 180 |
| ggcgcggggc gatactcccc gcagctgcac ccgcatttcc agagcgcgat gcagcattac | 240 |
| agccagaaga gcgaggtgta tccgttcacc cagctgaaat tcaagagcca tgtccagcag | 300 |
| aagctgaagc gggcgatgaa cgagttgtcg cccaggctga agagcatgg caaggaatcc | 360 |
| tttctccagt tcgtcagccg ctaccagggc catgacagcg cggtgggcat gatccgctcc | 420 |
| atgggctacg acgcgctgtt cctgcccgac atctcggccg agatggccta cgacatcgtc | 480 |
| ggcaagcacc cggaaatcca gagcgtgacc gataacgacg ccaaccagtg gttcgcggcg | 540 |
| gaaacgggct tgcgggcct gatccagggc atcaaggcca aggtcaaggc tgccggcgcg | 600 |
| cgcttcagcc tgggttaccg gctgctgtcg gtgaggacgg acggcgacgg ctacctgctg | 660 |
| caactggccg cgacgacgg ctggaagctg aacaccgga cccgccatct gatcctggcc | 720 |
| attcctccgt cggcgatggc cgggctcaat gtcgacttcc ccgaggcgtg gagcggcgcg | 780 |
| cgctacggct cgctgccgct gttcaagggt ttcctcacct acggcgagcc atggtggctg | 840 |
| gactacaagc tggacgacca ggtgctgatc gtcgacaacc cgctgcgcaa gatctacttc | 900 |
| aagggcgaca agtacctgtt cttctacacc gacagcgaga tggccaatta ctggcgcggc | 960 |
| tgcgtggccg aaggagagga cggctacctg gagcagatcc gcacccatct ggccagcgcg | 1020 |
| ctgggcatcg ttcgcgagcg cattccccag cccctcgccc atgtgcacaa gtattgggcg | 1080 |
| catggcgtgg agttctgccg cgacagcgat atcgaccatc cgtccgcgct cagccaccgc | 1140 |
| gacagcggca tcatcgcctg ttcggacgcc tacaccgagc actgcggctg gatggagggc | 1200 |
| ggcctgctca gcgcccgcga agccagccgt ctgctgctgc agcgcatcgc cgcg | 1254 |

<210> SEQ ID NO 2
<211> LENGTH: 418
<212> TYPE: PRT
<213> ORGANISM: Chromobacterium violaceum

<400> SEQUENCE: 2

Met Lys His Ser Ser Asp Ile Cys Ile Val Gly Ala Gly Ile Ser Gly
1               5                   10                  15

Leu Thr Cys Ala Ser His Leu Leu Asp Ser Pro Ala Cys Arg Gly Leu
            20                  25                  30

Ser Leu Arg Ile Phe Asp Met Gln Gln Glu Ala Gly Gly Arg Ile Arg
        35                  40                  45

Ser Lys Met Leu Asp Gly Lys Ala Ser Ile Glu Leu Gly Ala Gly Arg
    50                  55                  60

Tyr Ser Pro Gln Leu His Pro His Phe Gln Ser Ala Met Gln His Tyr
65                  70                  75                  80

Ser Gln Lys Ser Glu Val Tyr Pro Phe Thr Gln Leu Lys Phe Lys Ser
                85                  90                  95

His Val Gln Gln Lys Leu Lys Arg Ala Met Asn Glu Leu Ser Pro Arg

Leu Lys Glu His Gly Lys Glu Ser Phe Leu Gln Phe Val Ser Arg Tyr
           115                 120                 125

Gln Gly His Asp Ser Ala Val Gly Met Ile Arg Ser Met Gly Tyr Asp
       130                 135                 140

Ala Leu Phe Leu Pro Asp Ile Ser Ala Glu Met Ala Tyr Asp Ile Val
145                 150                 155                 160

Gly Lys His Pro Glu Ile Gln Ser Val Thr Asp Asn Asp Ala Asn Gln
                165                 170                 175

Trp Phe Ala Ala Glu Thr Gly Phe Ala Gly Leu Ile Gln Gly Ile Lys
               180                 185                 190

Ala Lys Val Lys Ala Ala Gly Ala Arg Phe Ser Leu Gly Tyr Arg Leu
           195                 200                 205

Leu Ser Val Arg Thr Asp Gly Asp Gly Tyr Leu Leu Gln Leu Ala Gly
       210                 215                 220

Asp Asp Gly Trp Lys Leu Glu His Arg Thr Arg His Leu Ile Leu Ala
225                 230                 235                 240

Ile Pro Pro Ser Ala Met Ala Gly Leu Asn Val Asp Phe Pro Glu Ala
                245                 250                 255

Trp Ser Gly Ala Arg Tyr Gly Ser Leu Pro Leu Phe Lys Gly Phe Leu
               260                 265                 270

Thr Tyr Gly Glu Pro Trp Trp Leu Asp Tyr Lys Leu Asp Asp Gln Val
           275                 280                 285

Leu Ile Val Asp Asn Pro Leu Arg Lys Ile Tyr Phe Lys Gly Asp Lys
       290                 295                 300

Tyr Leu Phe Phe Tyr Thr Asp Ser Glu Met Ala Asn Tyr Trp Arg Gly
305                 310                 315                 320

Cys Val Ala Glu Gly Glu Asp Gly Tyr Leu Glu Gln Ile Arg Thr His
                325                 330                 335

Leu Ala Ser Ala Leu Gly Ile Ala Arg Glu Arg Ile Pro Gln Pro Leu
               340                 345                 350

Ala His Val His Lys Tyr Trp Ala His Gly Val Glu Phe Cys Arg Asp
           355                 360                 365

Ser Asp Ile Asp His Pro Ser Ala Leu Ser His Arg Asp Ser Gly Ile
       370                 375                 380

Ile Ala Cys Ser Asp Ala Tyr Thr Glu His Cys Gly Trp Met Glu Gly
385                 390                 395                 400

Gly Leu Leu Ser Ala Arg Glu Ala Ser Arg Leu Leu Leu Gln Arg Ile
                405                 410                 415

Ala Ala

<210> SEQ ID NO 3
<211> LENGTH: 53
<212> TYPE: DNA
<213> ORGANISM: Artificial Sequence
<220> FEATURE:
<223> OTHER INFORMATION: Primer for amplifying TrpOX gene

<400> SEQUENCE: 3
gagatataca tatgcatcac catcaccatc acaagcattc ttccgatatc tgc       53

<210> SEQ ID NO 4
<211> LENGTH: 37
<212> TYPE: DNA
<213> ORGANISM: Artificial Sequence
<220> FEATURE:

```
<223> OTHER INFORMATION: Primer for amplifying TrpOX gene

<400> SEQUENCE: 4
gctgctgcag cgcatcgccg cgtaatgaaa gcttgcg                            37
```

TRYPTOPHAN OXIDASE AND USE THEREOF

This application is a Continuation of, and claims priority under 35 U.S.C. § 120 to, International Application No. PCT/JP2017/032917, filed Sep. 12, 2017, and claims priority therethrough under 35 U.S.C. § 119 to Japanese Patent Application No. 2016-177995, filed Sep. 12, 2016, the entireties of which are incorporated by reference herein. Also, the Sequence Listing filed electronically herewith is hereby incorporated by reference (File name: 2019-03-06T_US-591_Seq_List; File size: 6 KB; Date recorded: Mar. 6, 2019).

BACKGROUND OF THE INVENTION

Field of the Invention

The present invention relates to a tryptophan oxidase and use thereof.

Brief Description of the Related Art

Amino acids serve as important components of living bodies, and it is known that some amino acids can be indicators of various health conditions. Examples of a method for measuring amino acids include methods using instruments such as amino acid analyzers, high-performance liquid chromatography (HPLC), and liquid chromatography mass spectrometry (LC-MS) and methods for analyzing an amino acid using an enzyme that catalyzes a specific reaction for a specific amino acid. Japanese Patent No. 5212996 describes a method using a tryptophan oxidase to measure tryptophan, hence enzymatic methods for quantifying tryptophan are known.

However, these methods require the use of large-scale and expensive instruments, requiring expert knowledge and proficiency to maintain and operate the instruments, and hence, increasing the cost for their use. In addition, samples must be sequentially analyzed, increasing the time for analysis if many samples must be analyzed. In methods using the tryptophan oxidase, an oxidase having higher stability and activity would have many practical implications.

An aspect of the present invention is to provide a mutated tryptophan oxidase suitable for practical implementation.

SUMMARY OF INVENTION

Disclosed herein is a mutated tryptophan oxidase in which at least one amino acid residue of a wild-type tryptophan oxidase is mutated and the mutated tryptophan oxidase has higher tryptophan oxidase activity and/or stability than the wild-type tryptophan oxidase.

Also disclosed herein is the mutated tryptophan oxidase as described above, wherein the wild-type tryptophan oxidase has a motif selected from the group consisting of Motifs (2), (3), (5), (7), (9), (11), (13), (14), and combinations thereof; the mutated tryptophan oxidase comprises a mutation of at least one amino acid residue in a motif selected from the group consisting of Motifs (2), (3), (5), (7), (9), (11), (13), and (14): Motif (2): R64-Y65-S66-P67-Q68-L69-H70; Motif (3): Y87-P88-F89-T90; Motif (5): G142-Y143-D144-A145-L146; Motif (7): M155-A156-Y157-D158-I159; Motif (9): S264-L265; Motif (11): R296-K297-I298-Y299-F300-K301; Motif (13): G362-V363-E364-F365; Motif (14): H394-C395-G396-W397-M398-E399-G400.

Also disclosed herein is the mutated tryptophan oxidase as described above, comprising at least a mutation of Q68 in Motif (2).

Also disclosed herein is the mutated tryptophan oxidase as described above, wherein the mutation of Q68 is Q68C.

Also disclosed herein is the mutated tryptophan oxidase as described above, comprising at least a mutation of Y87 in Motif (3).

Also disclosed herein is the mutated tryptophan oxidase as described above, wherein the mutation of Y87 is Y87C.

Also disclosed herein is the mutated tryptophan oxidase as described above, comprising at least a mutation of A145 in Motif (5).

Also disclosed herein is the mutated tryptophan oxidase as described above, wherein the mutation of A145 is A145C, A145V, A145T, A145I, A145S, A145L, A145M, or A145Y.

Also disclosed herein is the mutated tryptophan oxidase as described above, comprising at least a mutation of M155 and/or I159 in Motif (7).

Also disclosed herein is the mutated tryptophan oxidase as described above, wherein the mutation of M155 is M155A, M155G, or M155V.

Also disclosed herein is the mutated tryptophan oxidase as described above, wherein the mutation of I159 is I159F.

Also disclosed herein is the mutated tryptophan oxidase as described above, comprising at least a mutation of L265 in Motif (9).

Also disclosed herein is the mutated tryptophan oxidase as described above, wherein the mutation of L265 is L265I or L265M.

Also disclosed herein is the mutated tryptophan oxidase as described above, comprising at least a mutation of R296 in Motif (11).

Also disclosed herein is the mutated tryptophan oxidase as described above, wherein the mutation of R296 is R296C.

Also disclosed herein is the mutated tryptophan oxidase as described above, comprising at least a mutation of V363 in Motif (13).

Also disclosed herein is the mutated tryptophan oxidase as described above, wherein the mutation of V363 is V363F, V363W, V363I, V363H, V363T, or V363C.

Also disclosed herein is the mutated tryptophan oxidase as described above, comprising at least a mutation of C395 in Motif (14).

Also disclosed herein is the mutated tryptophan oxidase as described above, wherein the mutation of C395 is C395S, C395A, C395P, C395Q, or C395Y.

Also disclosed herein is the mutated tryptophan oxidase as described above, wherein the wild-type tryptophan oxidase further has at least one motif selected from the group consisting of Motifs (1), (4), (6), (8), (10), and (12): Motif (1): E59-L60-G61; Motif (4): L102-K103; Motif (6): L148-P149; Motif (8): K162-H163-P164-E165; Motif (10): P266-L267-F268-K269-G270; Motif (12): F308-Y309.

Also disclosed herein is the mutated tryptophan oxidase as described above, wherein the wild-type tryptophan oxidase is a protein having: (a) an amino acid sequence represented by SEQ ID NO: 2; (b) an amino acid sequence comprising one or several amino acid residue substitutions, deletions, insertions, or additions in the amino acid sequence represented by SEQ ID NO: 2; or (c) an amino acid sequence having 90% or more identity to the amino acid sequence represented by SEQ ID NO: 2.

Also disclosed herein is the mutated tryptophan oxidase as described above, comprising a mutation of at least one amino acid residue selected from the group consisting of C29, S57, G63, L92, K95, A105, G136, E181, G190, C321, R367, Y80, G190, K83, H22, S409, N175, S84, F178, A179, V98, S140, M141, I166, T273, L352, and T310.

Also disclosed herein is the mutated tryptophan oxidase as described above, wherein the mutation of at least one amino acid residue is at least one mutation selected from the group consisting of C29V, S57T, G63Q, L92A, K95A, A105G, G136K, G136Q, G136R, G190C, C321S, C321A, and R367K.

Also disclosed herein is the mutated tryptophan oxidase as described above, wherein the mutation of at least one amino acid residue is at least one mutation selected from the group consisting of Y80C, G190C, K83C, E181C, H22C, S409C, N175C, S84C, F178C, A179C, V98C, S140C, M141C, I166C, T273C, L352C, and T310C.

Also disclosed herein is the mutated tryptophan oxidase as described above, wherein the mutation of at least one amino acid residue further comprises a mutation of at least one amino acid residue in a motif selected from the group consisting of Motifs (2), Also disclosed herein is the mutated tryptophan oxidase as described above, wherein at least one amino acid residue of Motif (2) is Q68, at least one amino acid residue of Motif (3) is Y87, at least one amino acid residue of Motif (11) is R296, at least one amino acid residue of Motif (13) is V363, or at least one amino acid residue of Motif (14) is G396.

Also disclosed herein is the mutated tryptophan oxidase as described above, wherein the mutation of at least one amino acid residue comprises at least one combination selected from Y80C/G190C, K83C/E181C, H22C/S409C, Q68C/N175C, S84C/F178C, Y87C/A179C, V98C/S140C, M141C/I166C, T273C/L352C, R296C/T310C, and V363C/G396C.

Also disclosed herein is a polynucleotide encoding the oxidase as described above.

Also disclosed herein is an expression vector comprising the polynucleotide as described above.

Also disclosed herein is a transformant comprising the expression vector as described above.

Also disclosed herein is a transformant as described above, wherein the transformant is a microorganism.

Also disclosed herein is the transformant as described above, wherein the microorganism is *Escherichia coli*.

Also disclosed herein is a kit for analyzing tryptophan, comprising the oxidase as described above.

Also disclosed herein is a kit for analyzing tryptophan as described above, further comprising at least one selected from the group consisting of a buffer solution or buffer salt for reaction, a hydrogen peroxide detection reagent.

Also disclosed herein is a method for detecting tryptophan in a sample, using the oxidase as described above.

Also disclosed herein is a method for producing a mutated tryptophan oxidase, using the transformant as described above.

Also disclosed herein is a detection system for analyzing tryptophan, comprising a device and the oxidase as described above.

Also disclosed herein is the detection system for analyzing tryptophan as described above, further comprising at least one selected from the group consisting of a buffer solution or buffer salt for reaction and a hydrogen peroxide detection reagent.

Also disclosed herein is an enzyme sensor for analyzing tryptophan, comprising an electrode for detection and the oxidase as described above fixed to or placed at the electrode for detection.

Disclosed herein is a mutated tryptophan oxidase having improved characteristics, such as increased activity and stability, relative to a wild-type tryptophan oxidase. Such an oxidase is useful for quick and highly sensitive measurement of tryptophan and/or production of tryptophan oxylate.

BRIEF DESCRIPTION OF THE DRAWING

FIG. 1. Diagram illustrating the residual activity of TrpOX incubated at each temperature for 15 minutes; A (circle): a wild-type TrpOX; B (square): TrpOX (C395A); C (triangle): TrpOX (S57T/Y80C/G136K/A145V/G190C/L265I/C395A).

DETAILED DESCRIPTION OF EXEMPLARY EMBODIMENTS

Described herein is a mutated tryptophan oxidase having at least one mutation, such as a modification, to a wild-type tryptophan oxidase. The mutated tryptophan oxidase has tryptophan oxidase activity. The tryptophan oxidase activity can result in a reversible reaction that generates tryptophan oxylate, which can be a 2-oxoacid obtained by substituting the amino acid tryptophan with a ketone group, ammonia, and hydrogen peroxide from tryptophan, normally L-tryptophan, water, and oxygen.

The wild-type tryptophan oxidase can mean a tryptophan oxidase before mutation. The wild-type tryptophan oxidase may be derived from or native to organisms, such as bacteria, actinomycetes, fungi, insects, fishes, animals, and plants. The wild-type tryptophan oxidase can be obtained by expressing a gene encoding a wild-type tryptophan oxidase heterologously, that is, using an organism, e.g., *Escherichia coli*, that does not intrinsically or natively have the gene. Examples of such organisms include *Streptomyces* bacteria such as *Streptomyces* sp.; *Chromobacterium* bacteria such as *Chromobacterium violaceum*; *Pseudogulbenkiania* bacteria such as *Pseudogulbenkiania ferrooxidans*; *Janthinobacterium* bacteria such as *Janthinobacterium lividum*, *Janthinobacterium agaricidamnosum*, and *Janthinobacterium* sp.; *Collimonas* bacteria such as *Collimonas* sp.; *Duganella* bacteria such as *Duganella* sp.; *Myxococcus* bacteria such as *Myxococcus stipitatus*; *Pseudoalteromonas* bacteria such as *Pseudoalteromonas tunicata*, *Pseudoalteromonas* sp., and *Pseudoalteromonas luteoviolacea*; and *gamma proteobacterium*.

Examples of the wild-type tryptophan oxidase can include a wild-type tryptophan oxidase having at least one of the following motifs: Motif (1) to Motif (14). A particular example is a wild-type tryptophan oxidase having at least one of the following Motifs (2), (3), (5), (7), (9), (11), (13), and (14). Such an oxidase can have one of Motifs (2), (3), (5), (7), (9), (11), (13), and (14) or a combination of two or more of these motifs, and ca includes Motif (14), or at least one or more of Motifs (5), (7), (9), (10) and (14), or can have all the motifs. The wild-type tryptophan oxidase can have at least one of Motifs (1), (4), (6), (8), (10), and (12), and can have all the motifs.

These Motifs are as follows:
Motif (1): E59-L60-G61
Motif (2): R64-Y65-S66-P67-Q68-L69-H70
Motif (3): Y87-P88-F89-T90
Motif (4): L102-K103
Motif (5): G142-Y143-D144-A145-L146
Motif (6): L148-P149
Motif (7): M155-A156-Y157-D158-I159
Motif (8): K162-H163-P164-E165
Motif (9): S264-L265
Motif (10): P266-L267-F268-K269-G270

Motif (11): R296-K297-I298-Y299-F300-K301
Motif (12): F308-Y309
Motif (13): G362-V363-E364-F365
Motif (14): H394-C395-G396-W397-M398-E399-G400

Each motif is determined by analysis of the amino acid sequence of SEQ ID NO: 2 and bacteria-derived tryptophan oxidases. The numbers of each motif represent amino acid residue numbers in the amino acid sequence represented by SEQ ID NO: 2, the details of which are as follows.

Motif (1) is the amino acid region in SEQ ID NO: 2 of glutamic acid (E59)-leucine (L60)-glycine (G61) at positions 59 to 61. Motif (2) is the amino acid region in SEQ ID NO: 2 of arginine (R64)-tyrosine (Y65)-serine (S66)-proline (P67)-glutamine (Q68)-leucine (L69)-histidine (H70) at positions 64 to 70. Motif (3) is the amino acid region of tyrosine (Y87)-proline (P88)-phenylalanine (F89)-threonine (T90) at positions 87 to 90 in SEQ ID NO: 2. Motif (5) is the amino acid region of glycine (G142)-tyrosine (Y143)-aspartic acid (D144)-alanine (A145)-leucine (L146) at positions 142 to 146 in SEQ ID NO: 2. Motif (6) is the amino acid region of leucine (L148)-proline (P149) at positions 148 to 149 in SEQ ID NO: 2. Motif (7) is the amino acid region of methionine (M155)-alanine (A156)-tyrosine (Y157)-aspartic acid (D158)-isoleucine (I159) at positions 155 to 159 in SEQ ID NO: 2. Motif (9) is the amino acid region of serine (S264)-leucine (L265) at positions 264 to 265 in SEQ ID NO: 2. Motif (11) is the amino acid region of arginine (R296)-lysine (K297)-isoleucine (I298)-tyrosine (Y299)-phenylalanine (F300)-lysine (K301) at positions 296 to 301 in SEQ ID NO: 2. Motif (14) is the amino acid region of histidine (H394)-cysteine (C395)-glycine (G396)-tryptophan (W397)-methionine (M398)-glutamic acid (E399)-glycine (G400) at positions 394-400 in SEQ ID NO: 2. These motifs can be determined by comparison analysis of the sequences of tryptophan oxidases derived from the respective organisms listed in Table 1. Table 1 also lists accession Nos. of tryptophan oxidase genes derived from the respective organisms and sequences corresponding to the respective motifs.

TABLE 2

| organism | Accession No. | Motif and corresponding residue No. | |
|---|---|---|---|
| | | Motif 4 | Motif 8 |
| Pseudogulbenkiania ferrooxidans | ERE19157.1 | 102-103 | 162-165 |
| Janthinobacterium lividum | ABK64067.1 | 102-103 | 162-165 |
| Collimonas sp. | ADU90703.1 | 102-103 | 162-165 |
| Janthinobacterium agaricidamnosum | CDG81735.1 | 102-103 | 162-165 |
| Duganella sp. | ACT67682.1 | 102-103 | 162-165 |
| Janthinobacterium sp. | ELX08822.1 | 115-116 | 175-178 |
| Pseudoalteromonas tunicata | EAR28037.1 | 102-103 | 162-165 |
| Pseudoalteromonas sp. | BAJ62029.1 | 102-103 | 162-165 |
| Pseudoalteromonas luteoviolacea | CCQ11959.1 | 102-103 | 162-165 |
| gamma proteobacterium | AFT64088.1 | 102-103 | 162-165 |

Motif (10) is a motif corresponding to an amino acid region of proline (P266)-leucine (L267)-phenylalanine (F268)-lysine (K269)-glycine (G270) at positions 266 to 270 of the amino acid sequence represented by SEQ ID NO: 2. Motif (12) is a motif corresponding to an amino acid region of phenylalanine (F308)-tyrosine (Y309) at positions 308 to 309 of the amino acid sequence represented by SEQ ID NO: 2. Motif (13) is a motif corresponding to an amino acid region of glycine (G362)-valine (V363)-glutamic acid (E364)-phenylalanine (F365) at positions 362 to 365 of the amino acid sequence represented by SEQ ID NO: 2. Motifs (10), (12), and (13) can be determined by comparison analysis of the sequences of tryptophan oxidases derived from the respective organisms listed in Table 3. Table 3 also lists accession Nos. of tryptophan oxidase genes derived from the respective organisms and sequence parts corresponding to the respective motifs.

TABLE 1

| organism | Accession No. | Motif and corresponding residue Nos. | | | | | | | | |
|---|---|---|---|---|---|---|---|---|---|---|
| | | Motif 1 | Motif 2 | Motif 3 | Motif 5 | Motif 6 | Motif 7 | Motif 9 | Motif 11 | Motif 14 |
| Pseudogulbenkiania ferrooxidans | ERE19157.1 | 59-61 | 64-70 | 87-90 | 142-146 | 148-149 | 155-159 | 264-265 | 296-301 | 394-400 |
| Janthinobacterium lividum | ABK64067.1 | 59-61 | 64-70 | 87-90 | 142-146 | 148-149 | 155-159 | 263-264 | 295-300 | 392-398 |
| Collimonas sp. | ADU90703.1 | 59-61 | 64-70 | 87-90 | 142-146 | 148-149 | 155-159 | 263-264 | 295-300 | 392-398 |
| Janthinobacterium agaricidamnosum | CDG81735.1 | 59-61 | 64-70 | 87-90 | 142-146 | 148-149 | 155-159 | 263-264 | 295-300 | 392-398 |
| Duganella sp. | ACT67682.1 | 59-61 | 64-70 | 87-90 | 142-146 | 148-149 | 155-159 | 263-264 | 295-300 | 392-398 |
| Janthinobacterium sp. | ELX08822.1 | 72-74 | 77-83 | 100-103 | 155-159 | 161-162 | 168-172 | 276-277 | 308-313 | 405-411 |

Motif (4) is the amino acid region of leucine (L102)-lysine (K103) at positions 102 to 103 in SEQ ID NO: 2. Motif (8) is the amino acid region of lysine (K162)-histidine (H163)-proline (P164)-glutamic acid (E165) at positions 162 to 165 in SEQ ID NO: 2. Motifs (4) and (8) can be determined by comparison analysis of the sequences of tryptophan oxidases derived from the respective organisms listed in Table 2. Table 2 also lists accession Nos. of tryptophan oxidase genes derived from the respective organisms and sequence parts corresponding to the respective motifs.

TABLE 3

| organism | Accession No. | Motif and corresponding residue No. | | |
|---|---|---|---|---|
| | | Motif 10 | Motif 12 | Motif 13 |
| Pseudogulbenkiania ferrooxidans | ERE19157.1 | 266-270 | 308-309 | 362-365 |
| Janthinobacterium lividum | ABK64067.1 | 265-269 | 307-308 | 361-364 |
| Collimonas sp. | ADU90703.1 | 265-269 | 307-308 | 361-364 |

TABLE 3-continued

| organism | Accession No. | Motif 10 | Motif 12 | Motif 13 |
|---|---|---|---|---|
| *Janthinobacterium agaricidamnosum* | CDG81735.1 | 265-269 | 307-308 | 361-364 |
| *Duganella* sp. | ACT67682.1 | 265-269 | 307-308 | 361-364 |
| *Janthinobacterium* sp. | ELX08822.1 | 278-282 | 320-321 | 374-377 |
| *Myxococcus stipitatus* | AGC43170.1 | 265-269 | 307-308 | 361-364 |
| *Pseudoalteromonas tunicata* | EAR28037.1 | 266-270 | 308-309 | 362-365 |
| *Pseudoalteromonas* sp. | BAJ62029.1 | 266-270 | 308-309 | 362-365 |
| *Pseudoalteromonas luteoviolacea* | CCQ11959.1 | 266-270 | 307-308 | 362-365 |
| gamma proteobacterium | AFT64088.1 | 266-270 | 308-309 | 362-365 |

The wild-type tryptophan oxidase may have any of the following amino acid sequences (a) to (c):

(a) the amino acid sequence represented by SEQ ID NO: 2;

(b) an amino acid sequence including one or several amino acid residue substitutions, deletions, insertions, or additions in the amino acid sequence represented by SEQ ID NO: 2; and/or (c) an amino acid sequence having 90% or more identity to the amino acid sequence represented by SEQ ID NO: 2.

The tryptophan oxidase shown in the amino acid sequence of SEQ ID NO: 2 is derived from or native to *Chromobacterium violaceum* and is encoded by the nucleic acid sequence of SEQ ID NO: 1, which is the full-length nucleic acid sequence of a wild-type tryptophan oxidase gene derived from or native to *Chromobacterium violaceum*.

The target amino acid residue for mutation such as substitution, deletion, insertion, or addition can be L-alanine (A), L-aspartic acid (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), or glycine (G), which are the natural L-α-amino acids. When the mutation is substitution, addition, or insertion, the amino acid residue to be substituted, added, or inserted is the same as the amino acid residue to be mutated as described above. L and α may be omitted in amino acid notation herein.

The amino acid sequence as described in the above (b) may include mutation, e.g., substitution, deletion, insertion, and addition, of one or several amino acid residues. The "one or several" can be 1 to 50, for example, 1 to 40, 1 to 30, 1 to 20, or 1 to 10, and include all numbers in between these ranges, such as. e.g., 1, 2, 3, 4, or 5.

The amino acid sequence as described in the above (c) may have at least 90% or more amino acid sequence identity to the amino acid sequence represented by SEQ ID NO: 2. The identity percentage of the amino acid sequence may be 92% or more, 95% or more, 97% or more, 98% or more, or 99% or more.

Proteins having the amino acid sequences as described in the above (b) and (c) can have an activity of 50% or more, 60% or more, 70% or more, 80% or more, 90% or more, or 95% or more of the tryptophan oxidase activity of a protein having the amino acid sequence as described in the above (a) when measured under the same condition.

The amino acid sequence identity can be determined using the algorithm BLAST by Karlin and Altschul (Pro. Natl. Acad. Sci. USA, 90, 5873 (1993)) or FASTA by Pearson (Methods Enzymol., 183, 63 (1990)), for example. Programs such as BLASTP have been developed based on this algorithm BLAST (see ncbi.nlm.nih.gov), and the amino acid sequence identity may be calculated using these programs with default settings. For amino acid sequence identity, a numerical value when, using the software GENETYX Ver. 7.0.9 by Genetyx Corporation employing the Lipman-Pearson method and using the full-length polypeptide encoded by ORF, similarity is calculated in terms of percentage with a setting of Unit Size to Compare of 2, for example. For the amino acid sequence identity, the smallest value among the values derived from these calculations may be employed.

The position(s) of the amino acid residue which can be mutated in the amino acid sequence of SEQ ID NO: 2 for preparation of (b) and (c) as described above will be obvious to the person or ordinary skill in the art; that is, the mutation can be introduced using amino acid sequences alignment for reference, for example. Specifically, the person of ordinary skill in the art can 1) compare a plurality of homologue amino acid sequences, e.g., the amino acid sequence of SEQ ID NO: 2 and homologue amino acid sequences, with each other, 2) determine relatively conserved regions and regions that are not relatively not conserved, and then 3) predict region(s) that can play or not play an important role for function from the relatively conserved region(s) and regions not relatively conserved, and can thus recognize structure-function correlation. Consequently, the person of ordinary skill in the art can determine the amino acid sequences of (b) and (c) in which mutation(s) of one or more amino acid residues that result in improved thermal stability can be introduced.

When mutation of an amino acid residue is introduced to the amino acid sequence represented by SEQ ID NO: 2 for preparation of (b) and (c) as described above, and when the mutation of the amino acid residue is substitution, such substitution of the amino acid residue may be a conservative substitution. The term "conservative substitution" can refer to substituting a certain amino acid residue with an amino acid residue having a similar side chain. Families of the amino acid residue having a similar side chain are well known in the art. Examples of such families can include amino acids having a basic side chain, e.g., lysine, arginine, and histidine; amino acids having an acidic side chain, e.g., aspartic acid and glutamic acid; amino acids having an uncharged polar side chain, e.g., asparagine, glutamine, serine, threonine, tyrosine, and cysteine; amino acids having a nonpolar side chain, e.g., glycine, alanine, valine, leucine, isoleucine, proline, phenylalanine, methionine, and tryptophan; amino acids having a β-position-branched side chain, e.g., threonine, valine, and isoleucine; amino acids having an aromatic side chain, e.g., tyrosine, phenylalanine, tryptophan, and histidine; amino acids having a hydroxy group, e.g., alcoholic- and phenolic-containing side chains, e.g., serine, threonine, and tyrosine; and amino acids having a sulfur-containing side chain, e.g., cysteine and methionine. The amino acids having an uncharged polar side chain and the amino acids having a nonpolar side chain may be collectively called neutral amino acids. The conservative substitution of the amino acid may be substitution between aspartic acid and glutamic acid, substitution among arginine, lysine, and histidine, substitution between tryptophan and phenylalanine, substitution between phenylalanine and valine, substitution among leucine, isoleucine, and alanine, and substitution between glycine and alanine.

The amino acid sequence of SEQ ID NO: 2 can include Motifs (1) to (14) shown in the first example. The amino acid sequences of (b) and (c) as described above also conserve at least one of Motifs (2), (3), (5), (7), (9), (11), (13), and (14); conserve Motifs (2), (3), (5), (7), (9), (11), (13), and (14); can include Motif (14), can have at least one or more of Motifs (5), (7), (9), and (10) and Motif (14), can have all the motifs. The wild-type tryptophan oxidase before mutation, or the tryptophan oxidase having any of (a) to (c) as describe above, for example, may further have at least one of Motifs (1), (4), (6), (8), (10), and (12); and can conserve Motifs (1) to (14).

The mutated tryptophan oxidase can be the wild-type tryptophan oxidase wherein at least one amino acid residue of which has been mutated.

The mutated tryptophan oxidase is normally improved in at least one characteristic thereof than the wild-type tryptophan oxidase before mutation. Examples of such a characteristic can include tryptophan oxidase activity and tryptophan oxidase stability, e.g., thermal stability. Either the tryptophan oxidase activity or the tryptophan oxidase stability, or both, can be improved as compared to the wild-type tryptophan oxidase. The improvement in the characteristics may be determined by comparing the wild-type tryptophan oxidase and the mutated tryptophan oxidase in activity at a certain temperature using method of evaluation as described herein and calculating relative activity. The relative activity of the mutated tryptophan oxidase, with the activity of the wild-type one as 100%, can be more than 100%, or more than 101%, 103%, 104%, 105%, or 110%, or more than 120%, 130%, 140%, or 150%. Improvement in the tryptophan oxidase thermal stability can be determined by comparing the residual activity at a high temperature, that is, the residual activity after heating for 15 minutes at 40° C. or more, for example, or 45° C., 50° C., or 55° C., at a certain concentration of both the wild-type and mutated tryptophan oxidases, and calculating the relative residual activity. The residual activity of the mutated tryptophan oxidase, with the residual activity of the wild-type one as 100%, can be more than 100%, or more than 101%, 103%, 104%, 105%, 110%, 120%, 130%, or 140%, or more than 150%, 160%, 170%, or 180%.

Examples of the mutation of the amino acid of the mutated tryptophan oxidase can include deletion, substitution with another amino acid residue, and addition and insertion of at least one amino acid residue; it is normally substitution with another amino acid residue. The mutation of the amino acid residue may be introduced to one region in the amino acid sequence or introduced to a plurality of different regions. The number of mutation(s) in the mutated tryptophan oxidase may be at least one, and can be 1 to 100, 1 to 80, 1 to 50, 1 to 30, 1 to 20, 1 to 10, or 1 to 5.

When the wild-type tryptophan oxidase includes at least one of Motifs (2), (3), (5), (7), (9), (11), (13), and (14), at least one amino acid residue in these motifs can be mutated. That is, the mutated tryptophan oxidase can have one or more mutation of one amino acid residue or a combination of mutations of two or more amino acid residues in Motif (5), mutation of one amino acid residue or a combination of mutations of two or more amino acid residues in Motif (7), mutation of one amino acid residue or a combination of mutations of two or more amino acid residues in Motif (9), mutation of one amino acid residue or a combination of mutations of two or more amino acid residues in Motif (13), and mutation of one amino acid residue or a combination of mutations of two or more amino acid residues in Motif (14).

The mutated tryptophan oxidase can include mutation of at least one amino acid residue in Motif (14) or can include mutation of one or more of at least one amino acid residue in Motif (5), at least one amino acid residue in Motif (7), and at least one amino acid residue in Motif (9), mutation of one or more of at least one amino acid residue in Motif (11), mutation of one or more of at least one amino acid residue in Motif (13), and mutation of at least one amino acid residue in Motif (14) and can include mutation of one or more of at least one amino acid residue in Motif (5) and at least one amino acid residue in Motif (9) and mutation of at least one amino acid residue in Motif (14).

The mutated tryptophan oxidase can include mutation of at least one amino acid residue in Motif (14), e.g., mutation of C395, or can include a combination of mutation(s) of at least one amino acid residue in Motif (14), e.g., mutation of C395, and another mutation.

The mutation of the amino acid residues included in Motif (2) can include mutation of Q68. The mutation of Q68 can be substitution with cysteine (Q68C). Q68C can form an SS bond with another cysteine residue.

The mutation of the amino acid residues included in Motif (3) can include mutation of Y87. The mutation of Y87 can be substitution with cysteine (Y87C).

The mutation of the amino acid residues included in Motif (5) can include mutation of A145. The mutation of A145 can be substitution with cysteine, valine, threonine, isoleucine, serine, leucine, methionine, or tyrosine (A145C, A145V, A145T, A145I, A145S, A145L, A145M, or A145Y), or A145C or A145V, and a particular example is A145V.

The mutation of the amino acid residues included in Motif (7) can include mutation of M155 and/or mutation of I159 particularly can include mutation of M155. The mutation of M155 can be substitution with alanine, glycine, or valine (M155A, M155G, or M155V) and particularly can be M155A. The mutation of I159 can be substitution with phenylalanine (I159F).

The mutation of the amino acid residues included in Motif (9) can include mutation of L265. The mutation of L265 can be substitution with isoleucine (L265I) or substitution with methionine (L265M) and particularly can be L265I.

The mutation of the amino acid residues included in Motif (11) can include mutation of R296. The mutation of R296 can be substitution with cysteine (R296C).

The mutation of the amino acid residues included in Motif (13) can include mutation of V363. The mutation of V363 can be substitution with phenylalanine, tryptophan, isoleucine, histidine, threonine, or cysteine (V363F, V363W, V363I, V363H, V363T, or V363C) and particularly can be V363F or V363W.

The mutation of the amino acid residues included in Motif (14) can include mutation of C395 or G396 and particularly can include mutation of C395. The mutation of C395 can be substitution with serine (C395S), substitution with alanine (C395A), substitution with histidine (C395H), substitution with proline (C395P), substitution with glutamine (C395Q), substitution with threonine (C395T), substitution with methionine (C395M), substitution with glycine (C395G), substitution with phenylalanine (C395F), substitution with tyrosine (C395Y), substitution with aspartic acid (C395D), substitution with glutamic acid (C395E), substitution with lysine (C395K), substitution with asparagine (C395N), substitution with arginine (C395R), or substitution with valine (C395V), and particularly can be C395S, C395A, C395P, C395Q, or C395Y. The mutation of G396 can be substitution with cysteine (G396C).

The mutated tryptophan oxidase may have an SS bond by mutation of at least one amino acid residue in the motifs, or by mutation of amino acid residues in one or more of Motifs (2), (3), (11), (13), and (14). Examples of mutation of SS bond introduction can include Q68C (Motif (2)), Y87C (Motif (3)), R296C (Motif (11)), C363C (Motif (13)), and G396C (Motif (14)); among these, the mutation of C363C/G396C is introduced, whereby an SS bond can be formed between both.

Exemplary mutation sites in the tryptophan oxidase having any of (a) to (c) can be cysteine at position 29 (C29), serine at position 57 (S57), glycine at position 63 (G63), leucine at position 92 (L92), lysine at position 95 (K95), alanine at position 105 (A105), glycine at position 136 (G136), glutamic acid at position 181 (E181), glycine at position 190 (G190), cysteine at position 321 (C321), arginine at position 367 (R367), lysine at position 83 (K83), tyrosine at position 80 (Y80), glycine at position 190 (G190), histidine at position 22 (H22), serine at position 409 (S409), asparagine at position 175 (N175), serine at position 84 (S84), phenylalanine at position 178 (F178), alanine at position 179 (A179), valine at position 98 (V98), serine at position 140 (S140), methionine at position 141 (M141), isoleucine at position 166 (I166), tryptophan at position 273 (T273), leucine at position 352 (L352), and threonine at position 310 (T310) in the amino acid sequence of SEQ ID NO: 2. The mutation may be one mutation as described above or a combination of two or more.

Mutation of C29, S57, G63, L92, K95, A105, G136, E181, G190, C321, and R367 can be substitution of each with another amino acid. The mutation of C29 can be substitution with valine (C29V). The mutation of S57 can be substitution with threonine, tryptophan, methionine, alanine, valine, tyrosine, cysteine, isoleucine, or leucine (S57T, S57W, S57M, S57A, S57V, S57Y, S57C, S57I, or S57L) and S57T is a particular example. The mutation of G63 can be substitution with glutamine (G63Q). The mutation of L92 can be substitution with alanine (L92A). The mutation of K95 can be substitution with alanine (K95A). The mutation of G136 can be substitution with lysine, glutamine, arginine, asparagine, or glutamic acid (G136K, G136Q, G136R, G136N, or G136E), and G136K is a particular example. The mutation of A105 can be substitution with glycine (A105G). The mutation of G190 can be substitution with cysteine (G190C). The mutation of C321 can be substitution with serine or alanine (C321S or C321A). The mutation of R367 can be substitution with lysine (R367K). The mutated tryptophan oxidase can include mutation of S57, G136, and G190.

Mutation of Y80, G190, K83, E181, H22, S409, N175, S84, F178, A179, V98, S140, M141, I166, T273, L352, or T310 can be substitution of each with cysteine. In addition to this mutation or independently thereof, the mutated tryptophan oxidase may have mutation of at least one amino acid residue in Motifs (2), (3), (11), (13), and (14, and can also have at least one substitution selected from Q68C (Motif (2)), Y87C (Motif (3)), R296C (Motif (11)), V363C (Motif (13)), and G396C (Motif (14)). By any of these, an SS bond can be introduced to between a cysteine residue after substitution and another cysteine residue or between cysteine residues after substitution, and as a result, the amount of free cysteine is reduced, by which stability can be improved. Examples of a combination of amino acid residues to which the bond is introduced can include Y80C/G190C, K83C/E181C, H22C/S409C, Q68C/N175C, S84C/F178C, Y87C/A179C, V98C/S140C, M141C/I166C, T273C/L352C, R296C/T310C, V363C/G396C (a combination of substitution of each with cysteine); Y80C/G190C and/or K83C/E181C are particular examples.

An amino acid residue after mutation may be substituted with an amino acid residue having a similar side chain. Examples of the amino acid residue having a similar side chain can include amino acids having a basic side chain, e.g., lysine, arginine, and histidine, amino acids having an acidic side chain, e.g., aspartic acid and glutamic acid, amino acids having an uncharged polar side chain, e.g., asparagine, glutamine, serine, threonine, tyrosine, and cysteine, amino acids having a nonpolar side chain, e.g., glycine, alanine, valine, leucine, isoleucine, proline, phenylalanine, methionine, and tryptophan, amino acids having a β-position-branched side chain, e.g., threonine, valine, and isoleucine, amino acid having an aromatic side chain, e.g., tyrosine, phenylalanine, tryptophan, and histidine, amino acids having a hydroxy group-containing side chain, e.g., alcohol and a phenoxy group-containing side chain, e.g., serine, threonine, and tyrosine, and amino acids having a sulfur-containing side chain, e.g., cysteine and methionine.

When the wild-type tryptophan oxidase before mutation has at least one of Motifs (2), (3), (5), (7), (9), (11), (13), and (14), the mutated tryptophan oxidase may have a combination of mutation of each Motif and the above point mutation, including the mutation of SS bond introduction.

Examples of a combination of two or more mutations in the tryptophan oxidase can include the following examples. In the following, Mutation Combination Examples 1 to 8 are exemplary, and Mutation Examples 1 and 2 are particularly exemplary.

Mutation Example 1

A combination of the following mutations:
mutation of at least one amino acid residue in Motif (5);
mutation of at least one amino acid residue in Motif (9);
mutation of at least one amino acid residue in Motif (14); and
a combination of at least one of mutation of S57, mutation of G136, mutation of Y80, mutation of G190, and mutation of R367 as needed, for example, S57T/Y80C/G136K/A145V/G190C/L265I/C395A, or S57T/Y80C/G136K/A145V/G190C/L265I/C395A.

Mutation Example 2

A combination of the following mutations:
mutation of at least one amino acid residue in Motif (5);
mutation of at least one amino acid residue in Motif (10);
mutation of at least one amino acid residue in Motif (14); and
a combination of at least one of mutation of S57, mutation of K83, and mutation of E181, for example, S57T/K83C/A145V/E181C/L265I/C395A.

Mutation Example 3

A combination of the following mutations:
mutation of at least one amino acid residue in Motif (14); and
a combination of at least one of mutation of H22, mutation of S57, mutation of G63, mutation of Y80, mutation of K83, mutation of S84, mutation of L92, mutation of K95, mutation of V98, mutation of A105, mutation of G136, mutation of S140, mutation of M141, mutation of I166, mutation of F178, mutation of E181, mutation of G190, mutation of T273, mutation of L352, mutation of R367, and mutation of S409 as needed, for example, S57T/C395A, K95A/C395A, R367K/C395A, G136K/C395A, G136Q/C395A, G136R/C395A, G63Q/C395A, A105G/C395A, L92A/C395A, S57T/G63Q/C395A, H22C/S409C/C395A, Y80C/G190C/C395A, K83C/E181C/C395A, S84C/F178C/ C395A, V98C/S140C/C395A, M141C/I166C/C395A, and T273C/L352C/C395A, and more preferably S57T/C395A, K95A/C395A, R367K/C395A, G136K/C395A, G63Q/ C395A, A105G/C395A, and L92A/C395A.

Mutation Example 4

A combination of the following mutations:
mutation of at least one amino acid residue in Motif (5);
mutation of at least one amino acid residue. in Motif (14); and
one or more of mutation of S57, mutation of G63, mutation of L92, mutation of K95, mutation of A105, and mutation of R367 as needed, for example, A145C/C395A, A145V/C395A, A145T/C395A, A145I/C395A, A145S/ C395A, A145L/C395A, A145M/C395A, A145Y/C395A, S57T/A145V/C395A, S57T/G63Q/A145V/C395A, S57T/ G63Q/G136K/A145V/C395A, G63Q/A145V/C395A, A105G/A145V/C395A, S57T/L92A/A145V/C395A, S57T/ A105G/A145V, S57T/K95A/A145V/C395A, S57T/K95A/ A145V/C395A, and S57T/G63Q/A145V/R367K/C395A, or A145C/C395A, A145V/C395A, S57T/A145V/C395A, S57T/G63Q/A145V/C395A, and S57T/G63Q/G136K/ A145V/C395A.

Mutation Example 5

A combination of the following mutations:
mutation of at least one amino acid residue in Motif (9);
mutation of at least one amino acid residue in Motif (14); and
mutation of S57 as needed, for example, L265I/C395A, L265M/C395A, or S57T/L265M/C395A, or L265I/C395A or L265M/C395A.

Mutation Example 6

A combination of the following mutations:
mutation of at least one amino acid residue in Motif (7);
mutation of at least one amino acid residue in Motif (9);
mutation of at least one amino acid residue in Motif (14); and
one or more of mutation of S57 and mutation of G136 as needed, for example, M155A/L265I/C395A, S57T/M155A/ L265I/C395A, or G136K/M155A/L265I/C395A, and more preferably M155A/L265I/C395A Mutation Example 7

A combination of the following mutations:
mutation of at least one amino acid residue in Motif (7);
mutation of at least one amino acid residue in Motif (14); and
at least one of mutation of L92 and mutation of K95 as needed, for example, I159F/C395A, M155A/C395A, M155G/C395A, M155V/C395A, L92A/M155A/C395A, or K95A/M155A/C395A, or I159F/C395A or M155A/C395A.

Mutation Example 8

A combination of the following mutations:
mutation of at least one amino acid residue in Motif (13);
mutation of at least one amino acid residue in Motif (14); and
mutation of S57 as needed, for example, V363W/C395A, V363F/C395A, V363I/C395A, V363H/C395A, V363T/ C395A, V363C/G396C/C395A, V363C/G396C/C395A, or S57T/V363W/C395A, or V363W/C395A or V363F/C395A Mutation Example 9

A combination of the following mutations:
mutation of at least one amino acid residue included in Motif (2);
mutation of at least one amino acid residue included in Motif (14); and
mutation of N175 as needed, for example, Q68C/N175C/ C395A.

Mutation Example 10

A combination of the following mutations:
mutation of A179
mutation of at least one amino acid residue in Motif (3); and
mutation of at least one amino acid residue in Motif (14), for example, Y87C/A179C/C395A.

Mutation Example 11

A combination of the following mutations:
mutation of at least one amino acid residue in Motif (11);
mutation of at least one amino acid residue in Motif (14); and
mutation of T310 as needed, for example, R296C/T310C/ C395A.

Mutation Example 12

A combination of the following mutations:
mutation of at least one amino acid residue in Motif (5);
mutation of at least one amino acid residue in Motif (7);
mutation of at least one amino acid residue in Motif (14); and
mutation of S57 as needed, for example, A145V/I159F/ C395A, A145C/M155A/C395A, S57T/A145V/I159F/ C395A, or S57T/A145V/M155A.

Mutation Example 13

A combination of the following mutations:
mutation of at least one amino acid residue included in Motif (5);
mutation of at least one amino acid residue in Motif (13);
mutation of at least one amino acid residue in Motif (14); and
at least one of mutation of S57 and mutation of G63 as needed, for example, A145V/V363W/C395A, S57T/ A145V/V363W/C395A, or S57T/G63Q/A145V/V363F/ C395A.

Mutation Example 14

A combination of the following mutations:
mutation of at least one amino acid residue in Motif (7);
mutation of at least one amino acid residue in Motif (9);
mutation of at least one amino acid residue in Motif (14); and
mutation of G63 as needed, for example G63Q/M155A/ L265I/C395A.

Mutation Example 15

A combination of the following mutations:
mutation of at least one amino acid residue in Motif (5);
mutation of at least one amino acid residue in Motif (7);
mutation of at least one amino acid residue in Motif (9); and
mutation of at least one amino acid residue in Motif (14), for example, A145V/M155A/L265I/C395A.

Mutation Example 16

A combination of the following mutations:
mutation of at least one amino acid residue in Motif (5);
mutation of at least one amino acid residue in Motif (9);
mutation of at least one amino acid residue in Motif (13);
mutation of at least one amino acid residue in Motif (14), and
mutation of S57 as needed, for example, S57T/A145V/L265I/V363F/C395A.

The mutated tryptophan oxidase may have another peptide component, e.g., a tag moiety, at its C-terminus or N-terminus. Examples of peptide components can include one that facilitates purification of a target protein, e.g., tag moieties such as a histidine tag and Strep-tag II; proteins generally used for the purification of a target protein such as glutathione-S-transferase and a maltose binding protein; one that improves the solubility of a target protein, e.g., Nus-tag; one that functions as a chaperon (e.g., Trigger Factor); and a linker that links with a protein or protein domain having another function or both. The mutated tryptophan oxidase may have an initiation methionine residue at its N-terminus.

The mutated tryptophan oxidase may have additional mutation(s), e.g., substitution, deletion, insertion, and addition, of one or several amino acid residues in addition to the above mutation so long as the characteristics described above are maintained. The number of the additional mutation(s) can be 1 to 100, for example, 1 to 50, 1 to 40, 1 to 30, 1 to 20, or 1 to 10, e.g., 1, 2, 3, 4, or 5. The person of ordinary skill in the art can produce such a mutated oxidase maintaining the characteristics described above as appropriate.

Consequently, the mutated tryptophan oxidase may be any of the following:

A mutated tryptophan oxidase including an amino acid sequence in which at least one amino acid residue in Motifs (2), (3), (5), (7), (9), (11), (13), and (14) is mutated (e.g., substituted) in an amino acid sequence of a tryptophan oxidase before mutation having at least one motif selected from the group consisting of Motifs (2), (3), (5), (7), (9), (11), (13), and (14) and having higher tryptophan oxidase activity and/or stability than the tryptophan oxidase before mutation, A mutated tryptophan oxidase having an amino acid sequence having additional mutation(s) of one or several amino acid residues in an amino acid sequence in which at least one of H22, C29, S57, G63, L92, K95, A105, G136, E181, G190, C321, R367, Y80, G190, K83, H22, S409, N175, S84, F178, A179, V98, S140, M141, I166, T273, L352, and T310 in an amino acid sequence of a tryptophan oxidase before mutation having (a) the amino acid sequence represented by SEQ ID NO: 2, (b) the amino acid sequence including one or several amino acid residue substitutions, deletions, insertions, or additions in the amino acid sequence represented by SEQ ID NO: 2, or (c) the amino acid sequence having 90% or more identity to the amino acid sequence represented by SEQ ID NO: 2 is mutated (e.g., substituted) and having higher tryptophan oxidase activity and/or stability than the tryptophan oxidase before mutation, and A mutated tryptophan oxidase including an amino acid sequence having additional mutation of one or several amino acid residues in an amino acid sequence in which at least one of H22, C29, S57, G63, L92, K95, A105, G136, E181, G190, C321, R367, Y80, G190, K83, H22, S409, N175, S84, F178, A179, V98, S140, M141, I166, T273, L352, and T310 and at least one amino acid residue in Motifs (2), (3), (5), (7), (9), (11), (13), and (14) in an amino acid sequence of a tryptophan oxidase before mutation having (a) the amino acid sequence represented by SEQ ID NO: 2, (b) the amino acid sequence including one or several amino acid residue substitutions, deletions, insertions, or additions in the amino acid sequence represented by SEQ ID NO: 2, or (c) the amino acid sequence having 90% or more identity to the amino acid sequence represented by SEQ ID NO: 2 and are mutated (e.g., substituted) and having higher tryptophan oxidase activity and/or stability than the tryptophan oxidase before mutation.

The mutated tryptophan oxidase has both the mutation and the additional mutation(s) described above and may thereby include an amino acid sequence having at least 90% or more amino acid sequence identity to the amino acid residue of the (wild-type) tryptophan oxidase before mutation. The identity percentage of the amino acid sequence may be 92% or more, 95% or more, 97% or more, 98% or more, or 99% or more. The definition and examples of the amino acid sequence identity are as described above.

Determination of the position of the amino acid residue to which the additional mutation can be introduced in the amino acid sequence is as described above. The part to which the additional mutation is introduced may be an amino acid residue in Motifs (2), (3), (5), (7), (9), (11), (13), and (14), and an amino acid residue other than H22, C29, S57, G63, L92, K95, A105, G136, E181, G190, C321, R367, Y80, G190, and K83.

When the additional mutation of the amino acid residue is substitution, such substitution of the amino acid residue may be a conservative substitution. The definition and examples of the term "conservative substitution" are as described above.

The mutated tryptophan oxidase can be prepared using a transformant expressing the mutated tryptophan oxidase or using a cell-free system or the like. The transformant expressing the mutated tryptophan oxidase can be produced by producing an expression vector including a polynucleotide encoding a polynucleotide encoding the mutated tryptophan oxidase and then introducing this expression vector into a host, for example. The polynucleotide encoding the mutated tryptophan oxidase may be DNA or RNA.

The expression vector may include the polynucleotide encoding the mutated tryptophan oxidase; examples thereof include cell system vectors expressing a protein in a host and cell-free system vectors using a protein translation system. The expression vector may also be a plasmid, a virus vector, a phage, an integrative vector, or an artificial chromosome. The integrative vector may be a vector which is entirely integrated into a genome of a host cell. Alternatively, the integrative vector may be a vector in which only a part, e.g., an expression unit including a polynucleotide encoding the mutated tryptophan oxidase as described herein and a promoter operably coupled thereto is integrated into a genome of a host cell. The expression vector may further be a DNA vector or an RNA vector.

The expression vector may further include regions encoding a promoter, a terminator, and a drug, e.g., tetracycline, ampicillin, kanamycin, hygromycin, and phosphinothricin, a resistance gene in addition to the polynucleotide encoding the mutated tryptophan oxidase. The expression vector may be a plasmid or an integrative vector. The expression vector may be a virus vector or a vector for a cell-free system. The expression vector may include a polynucleotide encoding another peptide component that can be added to the mutated tryptophan oxidase as described herein on the 3'- or 5'-terminal side relative to the polynucleotide encoding the mutated tryptophan oxidase. Examples of the polynucleotide encoding the other peptide component include a polynucleotide encoding the peptide component that facilitates purification of a target protein described above, a polynucleotide encoding the peptide component that improves the solubility of a target protein described above, a polynucleotide encoding a peptide component functioning as a chaperon, and a polynucleotide encoding a peptide component as a linker that links with a protein or protein domain having another function or both. Various expression vectors including the polynucleotide encoding the other peptide component can be used. Consequently, such expression vectors may be used in order to produce the expression vector including the polynucleotide encoding the mutated tryptophan oxidase; examples of the expression vectors include an expression vector including a polynucleotide encoding a peptide component that facilitates purification of a target protein, e.g., pET-15b, pET-51b, pET-41a, and pMAL-p5G, an expression vector including a polynucleotide encoding a peptide component that improves the solubility of a target protein, e.g., pET-50b, an expression vector including a polynucleotide encoding a peptide component functioning as a chaperon, e.g., pCold TF, and an expression vector including a polynucleotide coding a peptide component as a linker that links with a protein or protein domain having another function or both. The expression vector may include a region encoding a cleavage site by protease between the polynucleotide encoding the mutated tryptophan oxidase and the polynucleotide encoding the other peptide component. With this structure, cleavage between the mutated tryptophan oxidase and the other peptide component added thereto is enabled after protein expression.

Examples of the host for expressing the mutated tryptophan oxidase include various prokaryotic cells including *Escherichia* bacteria such as *Escherichia coli*, *Corynebacterium* bacteria, e.g., *Corynebacterium glutamicum*, and *Bacillus* bacteria, e.g., *Bacillus subtilis*; and various eukaryotic cells including *Saccharomyces* bacteria, e.g., *Saccharomyces cerevisiae*, *Pichia* bacteria, e.g., *Pichia stipitis*, and *Aspergillus* bacteria, e.g., *Aspergillus oryzae*. For the host, a strain depleting a certain gene may be used. Examples of the transformant include a transformant having an expression vector in cytoplasm and a transformant in which a target gene is introduced to a genome.

The transformant expressing the mutated tryptophan oxidase can be cultured in a culture medium having a composition described below, for example, using a certain culture apparatus, e.g., a test tube, a flask, and a jar fermenter. Culture conditions can be set as appropriate. Specifically, the culture temperature may be 10° C. to 37° C., pH may be 6.5 to 7.5, and the culture time may be 1 hour to 100 hours. Culture may be performed while dissolved oxygen concentration is controlled. In this case, a dissolved oxygen concentration (a DO value) in a culture liquid may be used as an indicator of control. Ventilation and stirring conditions can be controlled such that a relative dissolved oxygen concentration DO value with the oxygen concentration of the atmosphere as 21% does not fall below 1 to 10%, for example, or 3 to 8%. Culture may be batch culture or fed-batch culture. In the case of fed-batch culture, a solution as a sugar source or a solution containing phosphoric acid is added to the culture liquid in succession continuously or discontinuously, whereby culture can be continued.

The host to be transformed is as described above; *Escherichia coli* in detail can be selected from *Escherichia coli* JM 109 strain, DH5α strain, HB101 strain, BL21 (DE3) strain, and the like as subspecies of *Escherichia coli* K12 strain. A method for performing transformation and a method for selecting a transformant are described in Molecular Cloning: A Laboratory Manual, 3rd edition, Cold Spring Harbor press (2001/01/15), etc. The following describes a method for producing transformed *Escherichia coli* and producing a certain oxidase using the same as an example more specifically.

For a promoter expressing the polynucleotide encoding the mutated tryptophan oxidase, promoters that are normally used for heteroprotein production in *E. coli* can be used; examples thereof include strong promoters such as PhoA, PhoC, a T7 promoter, a lac promoter, a trp promoter, a trc promoter, a tac promoter, a PR promoter and a PL promoter of λ phage, and a T5 promoter, and PhoA, PhoC, and lac are particular examples. Examples of a vector include pUC, e.g., pUC19 and pUC18; pSTV, pBR, e.g., pBR322; pHSG, e.g., pHSG299, pHSG298, pHSG399, pHSG398; RSF, e.g., RSF1010; pACYC, e.g., pACYC177 and pACYC184; pMW, e.g., pMW119, pMW118, pMW219, and pMW218; pQE, e.g., pQE30; and derivatives thereof. A vector of phage DNA may be used as another vector. Further, an expression vector that includes a promoter and can express an insertion DNA sequence may be used. The vector can be pUC, pSTV, or pMW.

A terminator as a transcription termination sequence may be coupled to the downstream of the polynucleotide encoding the mutated tryptophan oxidase. Examples of such a terminator include a T7 terminator, an fd phage terminator, a T4 terminator, a terminator of a tetracycline resistance gene, and a terminator of *Escherichia coli* trpA gene.

A vector for introducing the polynucleotide encoding the mutated tryptophan oxidase into *Escherichia coli* can be a multicopy vector; examples thereof include plasmids having a ColE1-derived replication origin such as pUC type plasmids and pBR322 type plasmids and derivatives thereof. The "derivatives" can mean products with plasmids modified by substitution, depletion, insertion, and/or addition and the like of bases.

The vector can have a marker such as an ampicillin resistance gene in order to select a transformant. Expression vectors having a strong promoter are commercially available as such a plasmid.

*Escherichia coli* is transformed using the obtained expression vector, and this is cultured, whereby the mutated tryptophan oxidase can be obtained.

For a culture medium, culture media normally used for culturing *Escherichia coli* such as an M9-casamino acid culture medium and LB culture medium may be used. The culture medium may contain a certain carbon source, nitrogen source, and coenzyme, e.g., pyridoxine hydrochloride. Specifically, peptone, yeast extract, NaCl, glucose, $MgSO_4$, ammonium sulfate, potassium dihydrogenphosphate, ferric sulfate, manganese sulfate, and the like may be used. Culture conditions and production-inducing conditions are selected as appropriate in accordance with the types of the marker of the vector, the promoter, and the host bacteria used.

The mutated tryptophan oxidase is collected by the following method. After the transformant is collected, the mutated tryptophan oxidase can be obtained as a crushed object or a dissolved object by crushing, e.g., sonication and homogenization or dissolving, e.g., lysozyme treatment, bacterial cells. Such a crushed object and a dissolved object are subjected to techniques such as extraction, precipitation, filtration, and column chromatography, whereby the mutated tryptophan oxidase as described herein can be obtained.

The mutated tryptophan oxidase can be used for analysis of tryptophan. Such a method of analysis can include measurement of tryptophan contained in a sample using the mutated tryptophan oxidase.

The sample is not limited to a particular sample so long as it is a sample suspected to contain tryptophan; examples thereof include living body-derived samples, e.g., blood, urine, saliva, and tears, and foods and drinks, e.g., nutritional drinks and amino acid drinks. Tryptophan in the sample may be low in concentration, e.g., a concentration of less than 1 mM such as 1 µM or more and less than 1 mM, or high in concentration, e.g., a concentration of 1 mM or more such as 1 mM or more and less than 1 M.

The product that is detected in the analysis of tryptophan is not limited to a particular product so long as tryptophan can be measured and may be tryptophan oxylate, $NH_3$, or $H_2O_2$. Alternatively, a product of a coupled reaction as a result of being coupled with another reaction may be detected. Examples of such a coupled reaction include the following coupled reaction:

Tryptophan oxidation reaction:

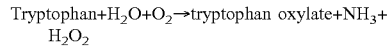

Tryptophan+$H_2O$+$O_2$→tryptophan oxylate+$NH_3$+$H_2O_2$

Coupled reaction: a reaction catalyzed by peroxidase

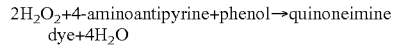

$2H_2O_2$+4-aminoantipyrine+phenol→quinoneimine dye+$4H_2O$

When the coupled reaction is used, measurement of tryptophan can be performed using 4-aminoantipyrine, phenol, and peroxidase in addition to the mutated tryptophan oxidase. Specifically, in an aqueous solution, e.g., a buffer solution, the sample is mixed with 4-aminoantipyrine, phenol, and peroxidase, then the mixed sample is subjected to the above oxidase reaction, and finally the absorbance (ca. 500 nm) of the produced quinoneimine dye is detected, whereby tryptophan is measured. The measurement can be performed qualitatively or quantitatively. The measurement may be performed based on the endpoint assay, which performs measurement until all substrates react, or performed based on the rate assay, the initial velocity assay, for example. The amount of oxygen required for the oxidation reaction is very small, and a required amount of oxygen can be covered by dissolved oxygen in the reaction system, and thus there is normally no need to additionally supply oxygen or a gas containing oxygen to the reaction system.

The mutated tryptophan oxidase does not react with amino acids other than tryptophan, e.g., L-α-amino acid, or has extremely low reactivity therewith. Consequently, even when a sample contains amino acids other than tryptophan, the amount of tryptophan in the sample can be specifically evaluated by using the mutated tryptophan oxidase.

The mutated tryptophan oxidase can be used for a hydrogen peroxide electrode. The amount of tryptophan in the sample can be specifically evaluated by using such a hydrogen peroxide electrode.

Further, the mutated tryptophan oxidase can be included in a kit for analyzing tryptophan. The kit for analyzing tryptophan can further include at least one of other reagents such as a buffer solution or buffer salt for reaction, a hydrogen peroxide detection reagent, an ammonia detection reagent, and a tryptophan oxylate detection reagent, such as an indole pyruvic acid detection reagent.

The buffer solution or buffer salt for reaction can be used in order to maintain pH in a reaction liquid at a value suitable for a target oxidase reaction.

The hydrogen peroxide detection reagent can be used when hydrogen peroxide is detected through color development, fluorescence, or the like, for example. Examples of such a reagent include a combination of peroxidase and a coloring agent that can be a substrate thereof; specific examples thereof include, but are not limited to, a combination of horseradish peroxidase, 4-aminoantipyrine, and phenol.

Examples of the ammonia detection reagent include the indophenol method combining phenol and hypochlorous acid.

Examples of the tryptophan oxalate detection reagent include 2-oxoacid dehydrogenase.

The mutated tryptophan oxidase can be a component of a detection system for analyzing tryptophan together with a device. The mutated tryptophan oxidase may be present as a unit independent of a micro device that can be supplied to the device in use or may be injected into, fixed to, or placed at the device in advance. The mutated tryptophan oxidase can be provided in the form of being injected into, fixed to, or placed at the device in advance. The tryptophan oxidase is fixed to or placed at the device directly or indirectly. For the device, a micro device such as a microchannel chip including a channel can be suitably used, for example.

The detection system for analyzing tryptophan may include other components. Examples of the other components can include a buffer solution or buffer salt for reaction, a hydrogen peroxide detection reagent, an ammonia detection reagent, and a tryptophan oxylate detection reagent. In the detection system for analyzing tryptophan, all the other components may be housed in the device. Alternatively, some of the components may be housed in the device, and others may be not being housed in the device, e.g., housed in another container. In this case, the components not housed in the device may be used by being injected into the device when a target substance is measured.

Examples of the device include 1) a device including a first zone for mixing a sample and the other components together to prepare a liquid mixture and a second zone for bringing the prepared liquid mixture into contact with the mutated tryptophan oxidase to detect tryptophan, that is, a device that performs mixing and detection processes in different zones; 2) a device including a zone for mixing a sample, the other components, and the mutated tryptophan oxidase together and detecting tryptophan by the mutated tryptophan oxidase, that is a device that performs mixing and detection processes in the same zone; and 3) a device including a channel that enables a sample, the other components, and the mutated tryptophan oxidase as needed, that is, to be mixed together and a zone for detecting tryptophan by the mutated tryptophan oxidase, that is, a device that, when the sample is injected into an injection port of the device, sends the liquid via the channel, automatically mixes the sample and the like together, and automatically detects tryptophan in the obtained liquid mixture in the detection zone. In view of automatization, preferred is the device of 3), especially the device of 3) in the form of a microchannel device. In the device of 3), the mutated tryptophan oxidase may be provided to the liquid flowing through the channel or provided in the form of being fixed to or placed at the detection zone and can be provided in the form of being fixed to or placed at the detection zone.

The mutated tryptophan oxidase can also be used as an enzyme sensor for analyzing tryptophan. The enzyme sensor for analyzing tryptophan includes an electrode for detection and the mutated tryptophan oxidase fixed to or placed at the electrode for detection, for example. The mutated tryptophan oxidase is fixed to or placed at the electrode directly or indirectly.

Examples of the electrode for detection include an electrode for detecting hydrogen peroxide, and more specific examples include an oxidase type electrode for detecting hydrogen peroxide and a diaphragm type electrode for detecting hydrogen peroxide. With this electrode, hydrogen peroxide occurring when tryptophan is oxidized through the tryptophan oxidase activity is detected, whereby analysis of tryptophan is enabled. For the other configuration, configurations employed for known sensors can be used as they are or in a modified manner as appropriate.

EXAMPLES

The following describes the present invention in more detail with reference to the following non-limiting examples Example 1: Expression and Purification of TrpOX A recombinant expression system of TrpOX using *Escherichia coli* was constructed. First, a plasmid for recombinant expression was constructed. A base sequence (SEQ ID NO: 1) of a TrpOX gene was amplified in accordance with a standard PCR method using a DNA primer 1 (SEQ ID NO: 3) and a DNA primer (SEQ ID NO: 4) to a target gene. Subsequently, the PCR product and pET24a (Merck Co., Ltd.) were digested with restriction enzymes NdeI (Takara Bio Inc.) and HindIII (Takara Bio Inc.), and proteins and unnecessary DNA fragments were removed using FastGene Plasmid Mini Kit (Nippon Genetics Co, Ltd.). The obtained product was subjected to ligation using Ligation High Ver. 2 (Toyobo Co., Ltd.), and a *Escherichia coli* XL-10 Gold transformed with the ligation product in accordance with a standard method. A plasmid was extracted from the transformant of the *Escherichia coli* XL-10 Gold, and insertion of the target gene into the plasmid was confirmed using a standard method of DNA sequence analysis. The plasmid into which the target gene was inserted was labelled pET24a-TrpOX, and BL21 (DE3) transformed with pET24a-TrpOX was labelled pET24a-TrpOX-BL21 (DE3).

TrpOX was prepared as follows. First, a glycerol stock of pET24a-TrpOX-BL21 (DE3) was inoculated onto an LB plate containing 50 μg/mL kanamycin and was stationary cultured at 37° C. overnight. A single colony from the LB plate was inoculated into 6 ml of an LB liquid culture medium containing 50 μg/mL kanamycin in a 50 mL tube, and was cultured at 37° C. by gyratory shaking until a value of OD600 reached about 0.6. Subsequently, the single colony was allowed to stand at 16° C. for 30 minutes, and IPTG was added to a final concentration of 1.0 mM. The single colony was cultured at 16° C. overnight with gyratory shaking, and then transferred to a 2.0 ml tube. The bacterial cells were suspended with a lysis buffer (50 mM Tris-HCl, 500 mM NaCl, 75 mM imidazole, and pH 8.0) and were sonicated using an ultrasonic crusher (BIORUPTER, Cosmo Bio Co., Ltd.) twice at intervals of 30 seconds for 10 minutes under the operation mode of "H" strength. The extract was centrifuged at 13,000×g for 15 minutes, and the supernatant was collected and purified using His Spin Trap (GE Healthcare Japan Corporation) or TALON Spin Columns (Takara Bio Inc.). Purification was performed in accordance with the product protocols. When His Spin Trap was used, a washing buffer (50 mM Tris-HCl, 500 mM NaCl, 75 mM imidazole, pH 8.0) and an elution buffer (50 mM Tris-HCl, 500 mM NaCl, 500 mM imidazole, pH 8.0) were used. When TALON Spin Columns was used, a lysis buffer and a washing buffer (50 mM Tris-HCl, 500 mM NaCl) and an elution buffer (50 mM Tris-HCl, 500 mM NaCl, 500 mM imidazole, pH 8.0) were used. Washing and elution were performed twice each, and the collected elution fractions were stored on ice.

Example 2: Preparation of TrpOX Mutant

A TrpOX mutant was prepared as follows. Using the QuickChange Lightning site-Directed Mutagenesis Kits (Agilent Technologies), mutation introduction to a TrpOX gene was performed in accordance with the protocol attached to the product using pET28a-TrpOX as a template. When multiple mutations were introduced, a mutation was added to a plasmid that already had a mutation introduced, and used as a template. Using this mutated plasmid, recombinant expression and purification were performed in accordance with the method described in Example 1, whereby various TrpOX mutants were acquired.

Example 3: Evaluation of Activity and Thermal Stability (1)

The activity and thermal stability of the wild-type TrpOX and the TrpOX mutants prepared in Examples 1 and 2 were evaluated in accordance with the following procedure. TrpOX was dispensed to a microtube in a concentration of 0.1 mg/ml, and incubated at a temperature of either 4° C. or 45° C. for 15 minutes, and diluted with 100 mM Tris-HCl, pH 8.0 to a final concentration of 0.02 mg/ml.

The following Reaction Liquids A and B were prepared.
Reaction Liquid A: 2 mM phenol, 200 mM Tris-HCl, pH 8.0
Reaction Liquid B: 100 mM 4-aminoantipyrine, 1500 U/ml peroxidase Temporal changes in the absorbance at a wavelength of 505 nm of a solution obtained by adding 10 μl of at 0.02 mg/ml TrpOX to a solution of 49 μl of Reaction Liquid A, 2 μl of Reaction Liquid B, 29 μl of ultrapure water, and 10 μl of 0.1 M Trp in a 96-well microplate were measured with a microplate reader (xMark Microplate Spectrophotometer, Bio-Rad Laboratories, Inc.). Table 4 lists the relative activities and residual activities of TrpOX mutants. In Table 4, relative activity compared with control is the ratio of the activity of each TrpOX mutant after treating at 4° C. for 15 minutes to the activity of the control (the wild-type TrpOX) after treating at 4° C. for 15 minutes that is set to 100%. In Table 4, residual activity after heat treatment is the ratio of the activity of each TrpOX mutant after heat treatment (15 minutes treatment at 45° C.) to the activity of each TrpOX after treating at 4° C. for 15 minutes that is set to 100%.

Tables 5 and 6 list the relative activities and residual activities of TrpOX mutants obtained by introducing mutation with a gene of TrpOX (C395A) as a template. The TrpOX mutants in Table 6 are mutants obtained by introducing mutation aiming at introduction of an S—S bond to TrpOX (C395A). In Tables 5 and 6, relative activity compared with control is the ratio of the activity of each TrpOX mutant after treating at 4° C. for 15 minutes to the activity of the control (TrpOX (C395A)) after treating at 4° C. for 15 minutes that is set to 100%. Residual activity after heat treatment is the ratio of the activity of each TrpOX mutant after heat treatment (15 minutes treatment at 45° C.) to the activity of each TrpOX mutant after treating at 4° C. for 15 minutes that is set to 100%. The control in Table 4 is a result of the wild-type one, and the control in each of Tables 5 and 6 is a result of TrpOX (C395A).

TABLE 4

Relative activity and residual activity of wild-type TrpOX and TrpOX mutants

| Mutation introduced to wild-type TrpOX | Relative activity compared with control | Residual activity after 45° C., 15 minutes heat treatment |
| --- | --- | --- |
| WT | 100% | 15% |
| C29V | 117% | 9% |
| S57T | 144% | 38% |
| G63Q | 123% | 13% |
| G136K | 128% | 30% |
| A145V | 195% | 13% |
| A145C | 68% | 18% |
| M155A | 82% | 2% |
| L265M | 85% | 0% |
| L265I | 155% | 52% |
| C321S | 103% | 10% |
| C321A | 62% | 19% |
| V363W | 43% | 18% |
| C395S | 121% | 5% |
| C395A | 194% | 45% |

TABLE 5

Relative activity and residual activity of TrpOX mutants

| Mutation introduced to TrpOX (C395A) | Relative activity compared with control | Residual activity after 45° C., 15 minutes heat treatment |
| --- | --- | --- |
| control | 100% | 37% |
| S57T | 111% | 51% |
| S57W | 115% | 74% |
| S57M | 96% | 51% |
| S57A | 107% | 20% |
| S57V | 99% | 78% |
| S57Y | 99% | 39% |
| S57C | 102% | 19% |
| S57I | 99% | 74% |
| S57L | 97% | 54% |
| G63Q | 165% | 1% |
| L92A | 101% | 72% |
| K95A | 148% | 53% |
| A105G | 112% | 79% |
| G136Q | 116% | 81% |
| G136R | 124% | 81% |
| G136K | 124% | 76% |
| G136N | 103% | 30% |
| G136E | 90% | 46% |
| A145T | 119% | 6% |
| A145V | 131% | 36% |
| A145I | 104% | 45% |
| A145S | 110% | 66% |
| A145C | 123% | 71% |
| A145L | 70% | 46% |
| A145M | 70% | 53% |
| A145Y | 93% | 65% |
| M155A | 168% | 29% |
| M155G | 104% | 3% |
| M155V | 120% | 10% |
| I159F | 51% | 76% |
| L265I | 106% | 62% |
| L265M | 124% | 22% |
| V363W | 75% | 70% |

TABLE 5-continued

Relative activity and residual activity of TrpOX mutants

| Mutation introduced to TrpOX (C395A) | Relative activity compared with control | Residual activity after 45° C., 15 minutes heat treatment |
| --- | --- | --- |
| V363I | 81% | 46% |
| V363H | 112% | 18% |
| V363F | 105% | 76% |
| V363T | 112% | 7% |
| V363F | 133% | 53% |
| R367K | 138% | 61% |

TABLE 6

Relative activity and residual activity of TrpOX mutants

| Mutation introduced to TrpOX (C395A) | Relative activity compared with control | Residual activity after 45° C., 15 minutes heat treatment |
| --- | --- | --- |
| Control | 100% | 49% |
| H22C/S409C | 104% | 69% |
| Q68C/N175C | 88% | 53% |
| Y80C/G190C | 99% | 84% |
| K83C/E181C | 99% | 81% |
| S84C/F178C | 41% | 59% |
| Y87C/A179C | 13% | 53% |
| V98C/S140C | 94% | 67% |
| M141C/I166C | 85% | 66% |
| T273C/L352C | 123% | 22% |
| R296C/T310C | 71% | 67% |
| V363C/G396C | 46% | 57% |

Table 4 shows that the tryptophan oxidase activity and/or the thermal stability can be improved by mutation introduction to C29 (such as C29V), mutation introduction to S57 (such as S57T), mutation introduction to G63 (such as G63Q), mutation introduction to G136 (such as G136K), mutation introduction to Motif (5) (such as A145V), mutation introduction to Motif (9) (such as L265I), mutation introduction to C321 (such as C321A), mutation introduction to Motif (13) (such as V363W), and mutation introduction to Motif (14) (such as C395A).

It is revealed from the results of Table 5 that the tryptophan oxidase activity and/or the thermal stability can be improved by combining mutation introduction to S57 (such as S57T), mutation introduction to G136 (such as G136Q, G136R, and G136K), mutation introduction to Motif (5) (such as A145I, A145S, and A145C), mutation introduction to Motif (13) (such as V363F and V363I), mutation introduction to Motif (13) (such as V363W), mutation introduction to G63 (such as G63Q), mutation introduction to Motif (5) (such as A145T and A145V), and mutation introduction to Motif (7) (such as M155A, M155G, and M155V) and mutation introduction to Motif (14) (such as C395A).

It is revealed from the results of Table 6 that the tryptophan oxidase thermal stability can be improved and the tryptophan oxidase activity can also be improved by combining H22C/S409C, an amino acid residue in Motif (2) (such as Q68C)/N175C, Y80C/G190C, K83C/E181C, S84C/F178C, an amino acid residue from Motif (3) (such as Y87C)/A179C, V98C/S140C, M141C/I166C, T273C/L352C, an amino acid residue in Motif (13) (such as V363C)/G396C, or an amino acid residue in Motif (11) (such as R296C)/T310C and mutation introduction to Motif (14) (such as C395A). It is considered that an SS bond is introduced between cysteines after these combination mutations, thereby reducing the amount of free cysteine, and the characteristics of the tryptophan oxidase are improved.

Example 4: Preparation of TrpOX Multiple Mutant and Evaluation of Activity and Thermal Stability The expression of TrpOX prepared by introducing a plurality of mutation points to a target TrpOX by the method described in Example 2 was performed in accordance with the method described in Example 1. To purify TrpOX, first bacterial cells were inoculated onto an LB plate containing 50 µg/mL kanamycin and stationary cultured at 37° C. overnight. Then, the bacterial cells and 2 ml of an LB liquid culture medium containing 50 µg/ml kanamycin were cultured in a 12 ml tube at 37° C. with gyratory shaking. Subsequently, 1.5 ml of the culture liquid was added to a 150 ml flask containing LB liquid culture medium containing 50 µg/mL kanamycin and was cultured at 37° C. by gyratory shaking until a value of OD600 reached about 0.6. Subsequently, the bacterial cells were allowed to stand at 16° C. for 30 minutes, and IPTG was then added to a final concentration of 1.0 mM. The bacterial cells were cultured at 16° C. overnight by gyratory shaking, and then put into a 50 ml tube, washed with a bacterial cell washing buffer (50 mM Tris-HCl, 500 mM NaCl, pH 8.0), and then collected.

The bacterial cells were suspended with a lysis buffer (50 mM Tris-HCl, 500 mM NaCl, 20 mM imidazole, pH 8.0) and sonicated using an ultrasonic crusher (ISONATOR 201M, Kubota Corporation) at 180 W for 20 minutes. This extract was subjected to centrifugation at 15,000×g for 15 minutes, and the supernatant was collected, passed through a 0.22 µm filter, and purified using AKTA Explorer 10S and HisTrap FF crude 1 ml (GE Healthcare). The buffers were a column equilibration-and-washing buffer (50 mM Tris-HCl, 0.5 M NaCl, pH 8.0) and an elution buffer (50 mM Tris-HCl, 0.5 M NaCl, 500 mM imidazole, pH 8.0), and the flow rate was set to 1 mL/min. A sample was taken, then washed with the column equilibration-and-washing buffer, and eluted with 5 mL of a gradient with an imidazole concentration of 20 to 500 mM. 0.5 mL samples were collected, and the collected elution fractions were stored on ice.

Next, purification with an anion-exchange column was performed using AKTA Explorer 10S and HiTrap Q HP 1 mL. The buffers used for purification with HiTrap Q HP were column equilibration-and-washing buffer (50 mM Tris-HCl, pH 8.0) and an elution buffer (50 mM Tris-HCl, 1 M NaCl, pH 8.0), and the flow rate was set to 1 mL/min. Each sample was diluted 20 times with the equilibration-and-washing buffer, subjected to the anion-exchange column, and then washed with the column equilibration-and-washing buffer. Elution was performed with a 5 mL gradient with an NaCl concentration of 0 to 500 mM. 0.5 mL samples were collected, and the collected elution fractions were subjected to solution exchange with a dialysis buffer (100 mM Tris-HCl, 300 mM NaCl, pH 7.5) and stored at 4° C.

The activity and thermal stability was evaluated in accordance with the procedures described in Example 3, except that incubation was performed at 50° C. or 55° C. instead of 45° C. Table 7 lists the results of the evaluation of the activity and heat resistance of mutants to which a plurality of mutants were introduced with a gene of TrpOX (C395A) as a template. In Table 7, relative activity compared with control and residual activity after heat treatment have the same meanings as the respective ones in Tables 5 and 6 except that the temperature in the heat treatment is 50° C. or 55° C. The control in Table 7 is a result of TrpOX (C395A).

TABLE 7

Relative activity and residual activity of TrpOX mutants

| Mutation introduced to TrpOX (C395A) | Relative activity compared with control | Residual activity after each temperature, 15 minutes treatment | |
|---|---|---|---|
| | | 50° C. | 55° C. |
| control | 100% | 43% | 1% |
| S57T/G63Q | 91% | 83% | 3% |
| S57T/A145V | 135% | 78% | 2% |
| S57T/L265M | 116% | 53% | 1% |
| S57T/V363W | 73% | 84% | 2% |
| G63Q/A145V | 115% | 61% | 2% |
| A105G/A145V | 125% | 69% | 3% |
| A145V/I159F | 49% | 80% | 1% |
| A145V/L265M | 118% | 14% | 1% |
| A145V/V363W | 51% | 65% | 3% |
| L92A/M155A | 99% | 47% | 3% |
| K95A/M155A | 107% | 29% | 1% |
| A145C/M155A | 93% | 39% | 1% |
| M155A/L265I | 116% | 71% | 1% |
| S57T/G63Q/A145V | 120% | 86% | 3% |
| S57T/A105G/A145V | 129% | 89% | 9% |
| S57T/A145V/I159F | 55% | 93% | 27% |
| S57T/A145V/L265M | 122% | 59% | 4% |
| S57T/A145V/V363W | 58% | 86% | 6% |
| S57T/L92A/A145V | 121% | 92% | 11% |
| S57T/K95A/A145V | 128% | 80% | 5% |
| S57T/A145V/M155A | 125% | 71% | 2% |
| S57T/A145V/L265I | 132% | 96% | 11% |
| S57T/M155A/L265I | 106% | 90% | 7% |
| G136K/M155A/L265I | 106% | 84% | 5% |
| G63Q/M155A/L265I | 101% | 85% | 4% |
| A145V/M155A/L265I | 127% | 70% | 3% |
| S57T/G63Q/G136K/A145V | 117% | 93% | 27% |
| S57T/G63Q/A145V/V363F | 87% | 93% | 26% |
| S57T/G63Q/A145V/R367K | 119% | 91% | 9% |
| S57T/G136K/A145V/L265I | 122% | 93% | 51% |
| S57T/A145V/L265I/V363F | 83% | 95% | 47% |
| S57T/A145V/L265I/R367K | 121% | 94% | 30% |
| S57T/K83C/A145V/E181C/L265I | 135% | 98% | 75% |
| S57T/Y80C/G136K/A145V/G190C/L265I | 122% | 102% | 93% |

Table 7 shows that the mutated tryptophan oxidases shown in Mutation Examples 1 to 16 all have improved tryptophan oxidase activity and/or thermal stability.

Example 5: Evaluation of Activity and Thermal Stability (2)

Mutations listed in Table 8 were introduced to the wild-type TrpOX prepared in Example 1 in a manner similar to the preparation of mutants described in Example 2. The activity and thermal stability of each mutant were evaluated in a manner similar to that described in Example 3 except that incubation was performed at 50° C. instead of 45° C. Table 8 lists the relative activities and relative residual activities after heating at 50° C. for 15 minutes of the mutants. In Table 8, relative activity compared with control is the ratio of the activity of each TrpOX mutant after treating at 4° C. for 15 minutes to the activity of the control (the wild-type TrpOX) after treating at 4° C. for 15 minutes that is set to 100%. The relative residual activity is the ratio of the residual activity of each TrpOX mutant after heat treatment (15 minutes treatment at 50° C.) to the residual activity of the control (the wild-type TrpOX) after heat treatment (15 minutes treatment at 50° C.) that is set to 100%.

TABLE 8

Relative activity and residual activity of wild-type TrpOX and TrpOX mutants

| Mutation introduced to wild-type TrpOX | Relative activity compared with control | Relative residual activity after 50° C., 15 minutes treatment compared with control |
|---|---|---|
| WT | 100% | 100% |
| C395A | 344% | 253% |
| C395D | 124% | 21% |
| C395E | 127% | 64% |
| C395F | 195% | 195% |
| C395G | 290% | 128% |
| C395H | 311% | 137% |
| C395K | 131% | 57% |
| C395M | 331% | 96% |
| C395N | 211% | 80% |
| C395P | 380% | 208% |
| C395Q | 393% | 146% |
| C395R | 212% | 71% |
| C395T | 308% | 82% |
| C395V | 235% | 57% |
| C395Y | 184% | 221% |

Table 8 shows that the tryptophan oxidase activity can be improved by mutation introduction to Motif (14), and that the tryptophan oxidase activity and the thermal stability can be improved by mutation introduction in Motif (14), especially C395.

Example 6: Evaluation of Temperature Dependence

Temperature dependence for A) the wild-type TrpOX, B) TrpOX (C395A), and C) TrpOX (S57T/Y80C/G136K/A145V/G190C/L265I/C395A) were determined. Reaction and measurement were performed using a 96-well microplate. Each TrpOX sample prepared at 1.0 mg/ml was dispensed to a microtube, incubated at 4° C., 35° C., 40° C., 45° C., 50° C., 55° C., 60° C., 65° C., 70° C., 75° C., or 80° C. for 15 minutes, and, then, diluted with 100 mM Tris-HCl pH 8.0 to give 0.02 mg/ml of TrpOX. Using Reaction Liquid A and Reaction Liquid B of Example 3, temporal changes in the absorbance at a wavelength of 505 nm of a solution obtained by adding 10 µl of TrpOX prepared at 0.02 mg/ml to a solution obtained by mixing 49 µl of Reaction Liquid A, 2 µl of Reaction Liquid B, 29 µl of ultrapure water, and 10 µl of 0.1 M Trp together was measured with a microplate reader (xMark Microplate Spectrophotometer, Bio-Rad Laboratories, Inc.). FIG. 1 illustrates the residual activity of the oxidase incubated at each temperature after a lapse of a certain time. While the wild-type TrpOX showed a marked reduction in activity from 45° C. to 50° C., TrpOX (S57T/Y80C/G136K/A145V/G190C/L265I/C395A) showed high activity even after being incubated at 55° C., substantially improving thermal stability.

Example 7: Quantitative Analysis of Trp in Plasma

Using a TrpOX (S57T/G136K/A145V/L265I/C395A) mutant, Trp in human plasma was quantitatively analyzed. Reaction and measurement were performed using a 96-well plate at 37° C. The TrpOX (S57T/G136K/A145V/L265I/C395A) mutant was diluted so as to be 0.5 mg/ml with a 100 mM Tris-HCl pH 7.5 and a 300 mM NaCl solution. The following Reaction Liquid A and Reaction Liquid B were prepared.
Reaction Liquid A: 0.2 M HEPES pH 8.0
Reaction Liquid B: 100 mM TOOS, 100 mM 4-aminoantipyrine, 1,500 U/ml peroxidase, 2 M NaCl Preparation was performed so as to be 0.5 mg/ml relative to a solution obtained by adding 150 µl of Reaction Liquid A, 39 µl of Reaction Liquid B, 51 µl of ultrapure water, and 30 µl of a sample (an aqueous Trp solution or plasma) to a 96-well microplate. The amount of the sample added was adjusted in accordance with each dilution ratio (10 times, 20 times, and 25 times). Absorbance at 555 nm and 800 nm before adding and mixing 30 µl of TrpOX and after a certain time of mixing (Abs 555 nm (before), Abs 555 nm (after), Abs 800 nm (before), and Abs 800 nm (after)) were measured with a microplate reader (M2e, Molecular Devices).

Using the values of absorbance at respective measurement points before and after reaction, a change in the absorbance (ΔAbs) before and after addition of the oxidase liquid was determined to be (Abs 555 nm (after)-Abs 800 nm (after))–(Abs 555 nm (before)-Abs 800 nm (before))×270/300. A calibration curve was created from a relation between ΔAbs and a Trp concentration when the aqueous Trp solution was used as the sample, and a Trp concentration in human plasma was determined from ΔAbs when the human plasma was used as the sample. The calibration curve was created using an average when three experiments were performed for each Trp concentration, human plasma of the same lot was measured three times and was compared with an analysis value (45.4 µM) by an amino acid analyzer. Results are listed in Table 9.

TABLE 9

Rate of deviation between analysis result of Trp concentration in human plasma using mutated TrpOX and analysis value by amino acid analyzer

| | Dilution ratio | | |
|---|---|---|---|
| | x10 | x20 | x25 |
| Analysis value (µM) | 49.1 | 49.1 | 45.3 |
| SD | 0.9 | 2.1 | 3.1 |
| C.V. (%) | 1.7 | 4.3 | 6.9 |
| Rate of deviation (%) | 8.0 | 8.0 | −0.5 |

The results of the examples show that the mutated tryptophan oxidase improves the tryptophan oxidase activity compared with the wild-type and is thus useful for quick and highly sensitive measurement of tryptophan and/or production of tryptophan oxylate. Also shown is that the mutated tryptophan oxidase shows more favorable thermal stability than the wild-type one, can show favorable thermal stability especially in an aqueous solution, and is thus useful as a tryptophan test reagent, especially a liquid test reagent.

INDUSTRIAL APPLICABILITY

The present invention provides a mutated tryptophan oxidase useful for quick, highly sensitive, and specific measurement of tryptophan or production of tryptophan oxylate and use thereof. Consequently, the present invention is useful in various fields such as biological research, health and nutrition, medical treatment, and food manufacturing.

The invention claimed is:

1. A mutated tryptophan oxidase in which at least one amino acid residue of a wild-type tryptophan oxidase is mutated and the mutated tryptophan oxidase has higher tryptophan oxidase activity and/or stability than the wild-type tryptophan oxidase, wherein:
the wild-type tryptophan oxidase has Motif (14): H394-C395-G396-W397-M398-E399-G400 in an amino acid sequence represented by SEQ ID NO: 2; and
the mutated tryptophan oxidase comprises at least a mutation of C395 in Motif (14).

2. The mutated tryptophan oxidase according to claim 1, wherein
the wild-type tryptophan oxidase further has a motif selected from the group consisting of Motifs (2), (3), (5), (7), (9), (11), (13), (14), and combinations thereof in an amino acid sequence represented by SEQ ID NO: 2, and;
the mutated typtophan oxidase comprises a mutation of at least one amino acid residue in a motif selected from the group consisting of Motifs (2), (3), (5), (7), (9), (11), and (13):
Motif (2): R64-Y65-S66-P67-Q68-L69-H70
Motif (3): Y87-P88-F89-T90
Motif (5): G142-Y143-D144-A145-L146
Motif (7): M155-A156-Y157-D158-I159
Motif (9): 5264-L265
Motif (11): R296-K297-I298-Y299-F300-K301
Motif (13): G362-V363-E364-F365.

3. The mutated tryptophan oxidase according to claim 1, comprising at least a mutation of L265 in Motif (9).

4. The mutated tryptophan oxidase according to claim 3, wherein the mutation of L265 is L265I or L265M.

5. The mutated tryptophan oxidase according to claim 1, wherein the mutation of C395 is C395S, C395A, C395P, C395Q, or C395Y.

6. The mutated tryptophan oxidase according to claim 1, wherein the wild-type tryptophan oxidase further has at least one motif selected from the group consisting of Motifs (1), (4), (6), (8), (10), and (12):
Motif (1): E59-L60-G61
Motif (4): L102-K103
Motif (6): L148-P149
Motif (8): K162-H163-P164-E165
Motif (10): P266-L267-F268-K269-G270
Motif (12): F308-Y309.

7. The mutated tryptophan oxidase according to claim 1, wherein the wild-type tryptophan oxidase is a protein having:
(a) an amino acid sequence represented by SEQ ID NO: 2;
(b) an amino acid sequence comprising one or several amino acid residue substitutions, deletions, insertions, or additions in the amino acid sequence represented by SEQ ID NO: 2; or
(c) an amino acid sequence having 90% or more identity to the amino acid sequence represented by SEQ ID NO: 2.

8. The mutated tryptophan oxidase according to claim 1, comprising a mutation of an amino acid residue selected from the group consisting of C29, S57, G63, L92, K95, A105, G136, E181, G190, C321, 8367, Y80, G190, K83, H22, 5409, N175, S84, F178, A179, V98, 5140, M141, 1166, T273, L352, T310, and combinations thereof.

9. The mutated tryptophan oxidase according to claim 1, wherein the mutation of at least one amino acid residue further comprises a mutation of at least one amino acid residue in a motif selected from the group consisting of Motifs (2), (3), (11), (13), and (14), to cysteine.

10. The mutated tryptophan oxidase according to claim 9, wherein
at least one amino acid residue of Motif (2) is Q68,
at least one amino acid residue of Motif (3) is Y87,
at least one amino acid residue of Motif (11) is 8296,
at least one amino acid residue of Motif (13) is V363, or
at least one amino acid residue of Motif (14) is G396.

11. The mutated tryptophan oxidase according to claim 1, wherein the mutation of at least one amino acid residue comprises Y80C/G190C, K83C/E181C, H22C/S409C, Q68C/N175C, S84C/F178C, Y87C/A179C, V98C/S140C, M141C/I166C, T273C/L352C, R296C/T310C, and/or V363C/G396C.

12. A polynucleotide encoding the oxidase according to claim 1.

13. An expression vector comprising the polynucleotide according to claim 12.

14. A transformant comprising the expression vector according to claim 13.

15. A kit for analyzing tryptophan, comprising the oxidase according to claim 1.

16. A method for detecting tryptophan in a sample, using the oxidase according to claim 1.

17. A method for producing a mutated tryptophan oxidase, using the transformant according to claim 14.

18. A detection system for analyzing tryptophan, comprising a device and the oxidase according to claim 1.

19. An enzyme sensor for analyzing tryptophan, comprising an electrode for detection and the oxidase according to claim 1 fixed to or placed at the electrode for detection.

* * * * *